(12) United States Patent
Dalton et al.

(10) Patent No.: US 10,053,667 B2
(45) Date of Patent: Aug. 21, 2018

(54) DIFFERENTIATION OF HUMAN PLURIPOTENT STEM CELLS TO MULTIPOTENT NEURAL CREST CELLS

(71) Applicant: UNIVERSITY OF GEORGIA RESEARCH FOUNDATION, INC., Athens, GA (US)

(72) Inventors: Stephen Dalton, Athens, GA (US); Laura M. Menendez, Frederick, MD (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/000,382

(22) Filed: Jan. 19, 2016

(65) Prior Publication Data
US 2016/0237405 A1 Aug. 18, 2016

Related U.S. Application Data

(63) Continuation of application No. 13/977,387, filed as application No. PCT/US2011/065810 on Dec. 19, 2011, now abandoned.

(60) Provisional application No. 61/428,998, filed on Dec. 31, 2010, provisional application No. 61/429,344, filed on Jan. 3, 2011, provisional application No. 61/429,992, filed on Jan. 5, 2011, provisional application No. 61/548,045, filed on Oct. 17, 2011.

(51) Int. Cl.
*A61K 35/12* (2015.01)
*A01N 63/00* (2006.01)
*C12N 5/0797* (2010.01)

(52) U.S. Cl.
CPC ...... *C12N 5/0623* (2013.01); *C12N 2501/155* (2013.01); *C12N 2501/16* (2013.01); *C12N 2501/415* (2013.01); *C12N 2501/998* (2013.01); *C12N 2506/02* (2013.01); *C12N 2506/45* (2013.01)

(58) Field of Classification Search
USPC ....................................................... 424/93.7
See application file for complete search history.

(56) References Cited

U.S. PATENT DOCUMENTS

| 5,843,780 | A | 12/1998 | Thomson et al. |
| 2010/0034785 | A1 | 2/2010 | Pedersen et al. |
| 2010/0166713 | A1 | 7/2010 | Dalton et al. |
| 2013/0183674 | A1 | 7/2013 | Studer et al. |
| 2013/0336933 | A9 | 12/2013 | Jensen |

FOREIGN PATENT DOCUMENTS

| WO | 2008056166 A2 | 5/2008 |
| WO | 2010108005 A2 | 9/2010 |
| WO | 2010108008 A2 | 9/2010 |
| WO | 2012091978 A2 | 7/2012 |

OTHER PUBLICATIONS

Atilla-Gokcumen et al., Organometallic Compounds with Biological Activity: A Very Selective and Highly Potent Cellular Inhibitor for Glycogen Synthase Kinase 3 ChemBioChem 2006, 7, 1443-1450.*
Rieger R, et al. Glossary of Genetics Classical and Molecular, 5th Edition, Springer-Verlag, New York, 1991.
Tesar PJ, et al. New cell lines from mouse epiblast share defining features with human embryonic stem cells. Nature, 2007;448:196-203.
Takahashi K, et al. Induction of Pluripotent Stem Cells from Mouse Embryonic and adult Fibroblast Cultures by Defined Factors. Cell, 2006;126:663-676.
Thomson JA, et al. Embryonic Stem Cell Lines Derived from Human Blastocysts. Science, 1998;282:1145-1147.
Thomson JA, et al. Primate Embryonic Stem Cells. Current Topics in Development Biology, 1998;38:133-165.
Thomson JA, et al. Isolation of a Primate Embryonic Stem Cell Line. Proceedings of the National Academy of Sciences of the United States of America, 1995;92:7844-7848.
Ginis I, et al. Differences between human and mouse embryonic stem cells. Developmental Biology, 2004;269:360-380.
Draper JS, et al. Surface antigens of human embryonic stem cells: changes upon differentiation in culture. J Anat, 2002;200:249-258.
Carpenter MK, et al. Characterization and Differentiation of Human Embryonic Stem Cells. Cloning and Stem Cells, 2003;5:79-88.
Cooper S, et al. Biochemical properties of a keratan sulphate/chondroitin sulphate proteoglycan expressed in primate pluripotent stem cells. J Anat, 2002;200:259-265.
Oka M, et al. CD9 is Associated with Leukemia Inhibitory Factor-mediated Maintenance of Embryonic Stem Cells. Molecular Biology of the Cell, 2002;13:1274-1281.
Carpenter MK, et al. Properties of Four Human Embryonic Stem Cell Lines Maintained in a Feeder-free Culture System. Developmental Dynamics, 2004;229:243-258.

(Continued)

*Primary Examiner* — Maria G Leavitt
(74) *Attorney, Agent, or Firm* — Henry D. Coleman; R. Neil Sudol

(57) ABSTRACT

The present invention relates to the differentiation of human pluripotent cells, including human pluripotent stems cells to produce a self-renewing multipotent neural crest cell population in a single step method without the requirement of isolation of intermediate cells and without appreciable contamination (in certain preferred instances, virtually none) with Pax6+ neural progenitor cells in the population of p75+ Hnk1+ Ap2+ multipotent neural crest-like cells. The multipotent neural crest cell population obtained can be clonally amplified and maintained for >25 passages (>100 days) while retaining the capacity to differentiate into peripheral neurons, smooth muscle cells and mesenchymal precursor cells.

24 Claims, 14 Drawing Sheets

(56) References Cited

OTHER PUBLICATIONS

Lee G, et al. Derivation of neural crest cells from human pluripotent stem cells. Nature Protocols, 2010;5:688-701.
Selleck MA, Bronner-Fraser M. The genesis of avian neural crest cells: a classic embryonic induction. Proc Natl Acad Sci USA, 1996;93(18):9352-9357.
Meulemans D, Bronner-Fraser M. Gene-regulatory interactions in neural crest evolution and development. Dev Cell, 2004;7(3):291-299.
Garcia-Castro MI, et al. Ectodermal Wnt function as a neural crest inducer. Science, 2002;297(5582):848-851.
Patthey C, et al. Wnt-regulated temporal control of BMP exposure directs the choice between neural plate border and epidermal fate. Development, 2009;136(1):73-83.
Wilson SI, et al. The status of Wnt signaling regulates neural and epidermal fates in the chick embryo. Nature, 2001;411(6835):325-330.
Bonstein L, et al. Paraxial-fated mesoderm is required for neural crest induction in Xenopus embryos. Dev Biol, 1998;193(2):156-168.
Liem KF, et al. Dorsal differentiation of neural plate cells induced by BMP-mediated signals from epidermal ectoderm. Cell, 1995;82(6):969-979.
Monsoro-Burq AH, et al. Neural Crest induction by paraxial mesoderm in Xenopus embryos requires FGF signals. Development, 2003;130(14):3111-3124.
Marchant L, et al. The inductive properties of mesoderm suggest that the neural crest cells are specified by a BMP gradient. Dev Biol, 1998;198(2):319-329.
Labonne C, Bronner-Fraser M. Neural crest induction in Xenopus: evidence for a two-signal model. Development, 1998;125(13):2403-2414.
Koch P, et al. A rosette-type, self-renewing human ES cell-derived neural stem cell with potential for in vitro instruction and synaptic integration. Proc Natl Acad Sci USA, 2009;106(9):3225-3230.
Chambers SM, et al. Highly efficient neural conversion of human ES and iPS cells by dual inhibition of SMAD signaling. Nat Biotechnol, 2009;27(3):275-280.
Elkabetz Y, et al. Human ES cell-derived neural rosettes reveal a functionally distinct early neural stem cell stage. Genes Dev, 2008;22(2):152-165.
Li XJ, et al. Specification of motoneurons from human embryonic stem cells. Nat Biotechnol, 2005;23(2):215-221.
Lee G, et al. Isolation and directed differentiation of neural crest stem cells derived from human embryonic stem cells. Nat Biotechnol, 2007;25(12):1468-1475.
Lee G, Studer L. Induced pluripotent stem cell technology for the study of human disease. Nat Methods, 2010;7(1):25-27.
Jiang X, et al. Isolation and characterization of neural crest stem cells derived from in vitro-differentiated human embryonic stem cells. Stem Cells Dev, 2009;18(7):1059-1070.
Lee G, et al. Derivation of neural crest cells from human pluripotent stem cells. Nat Protoc, 2010;5(4):688-701.
Meijer L, et al. Pharmacological inhibitors of glycogen synthase kinase 3. Trends Pharmacol Sci, 2004;25(9):471-480.
Sato N, et al. Maintenance of pluripotency in human and mouse embryonic stem cells through activation of Wnt signaling by a pharmacological GSK-3-specific inhibitor. Nat Med, 2004;10(1):55-63.
Barberi T, et al. Derivation of multipotent mesenchymal precursors from human embryonic stem cells. PLoS Med, 2005;2(6):e161.
Barberi T, et al. Derivation of engraftable skeletal myoblasts from human embryonic stem cells. Nat Med, 2007;13(5):642-648.
Zhou Y, Snead ML. Derivation of cranial neural crest-like cells from human embryonic stem cells. Biochem Biophys Res Commun, 2008;276(3):542-547.
Singh AM, et al. Chibby, an antagonist of the Wnt/beta-catenin pathway, facilitates cardiomyocyte differentiation of murine embryonic stem cells. Circulation, 2007;115(5):617-626.
Darnell DK, et al. Dynamic labeling techniques for fate mapping, testing cell commitment, and following living cells in avian embryos. Methods Mol Biol, 2000;135:305-321.
Mizuseki, et al. Generation of neural crest-derived peripheral neurons and floor plate cells from mouse and primate embryonic stem cells. Proceedings of the National Academy of Sciences USA, 2003;100(10):5828-2833.
Li, et al. Generation of Human-Induced Pluripotent Stem Cells in the Absence of Exogenous Sox2. Stem Cells, 2009;27(12):2992-3000.
Kim, et al. Robust Enhancement of Neural Differentiation from Human ES and iPS Cells Regardless of their Innate Difference in Differentiation Propensity. Stem Cell, 2010;6:270-281.
Chambers SM, et al. Highly efficient neural conversion of human ES and IPS cells by dual inhibition of SMAD signaling, Nature Biotechnology, 2009;27:275-280.
Menendez L, et al. Wnt signaling and a Smad pathway blockade direct the differentiation of human pluripotent stem cells to multipotent neural crest cells. Proceedings of the national Academy of Sciences, 2011;108:19240-19245.
Dae-Sung K, et al. Robust enhancement of neural differentiation from human ES and IPS cells regardless of their innate difference in differentiation propensity. Stem Cell Reviews and Reports, 2010;6:270-281.
Gabsang L, et al. Isolation and directed differentiation of neural crest stem cells derived from human embryonic stem cells. 20071201;20071125, 2007;25:1468-1475.
Sandell LL, Trainor PA. Neural crest cell plasticity. Size Matters. Adv Exp Med Bid, 2006;589:1-248.
Salinas, et al. Wnt Signaling in Neural Circuit Assembly. Annu Rev Neurosci, 2008;32:339-358.
Xiao, et al. Activin A Maintains Self-Renewal and Regulates Fibroblast Growth Factor, Wnt, and Bone Morphogenic Protein Pathways in Human Embryonic Stem Cells. TEM Cells, 2006;24:1476-1486.

\* cited by examiner

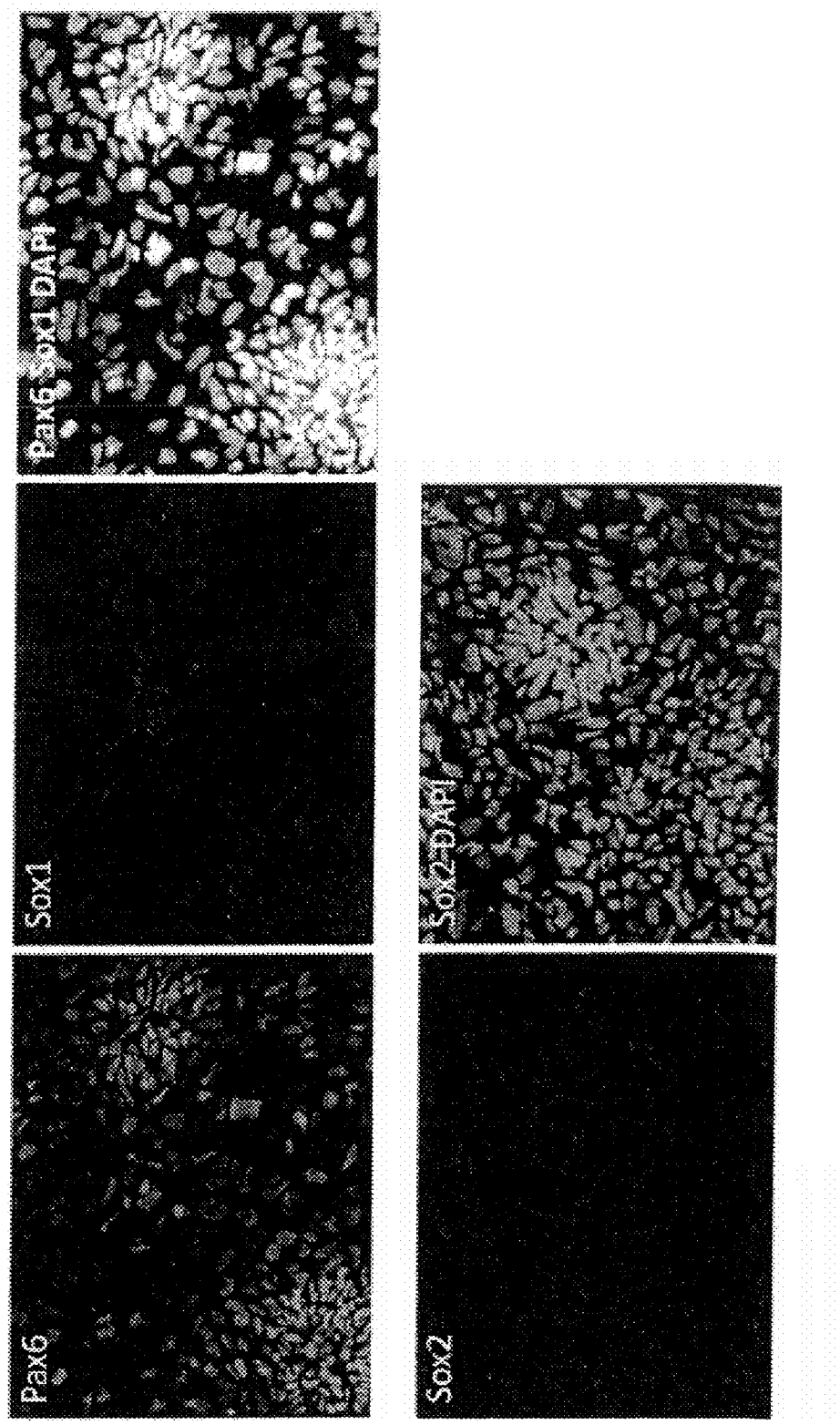
FIGURE 7 (Fig. S1)

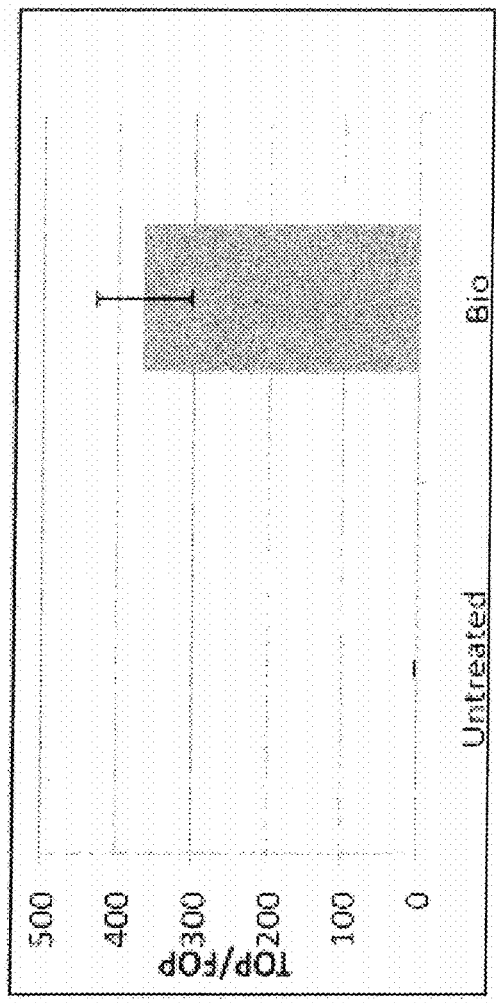
FIGURE 8 (Fig. S2)

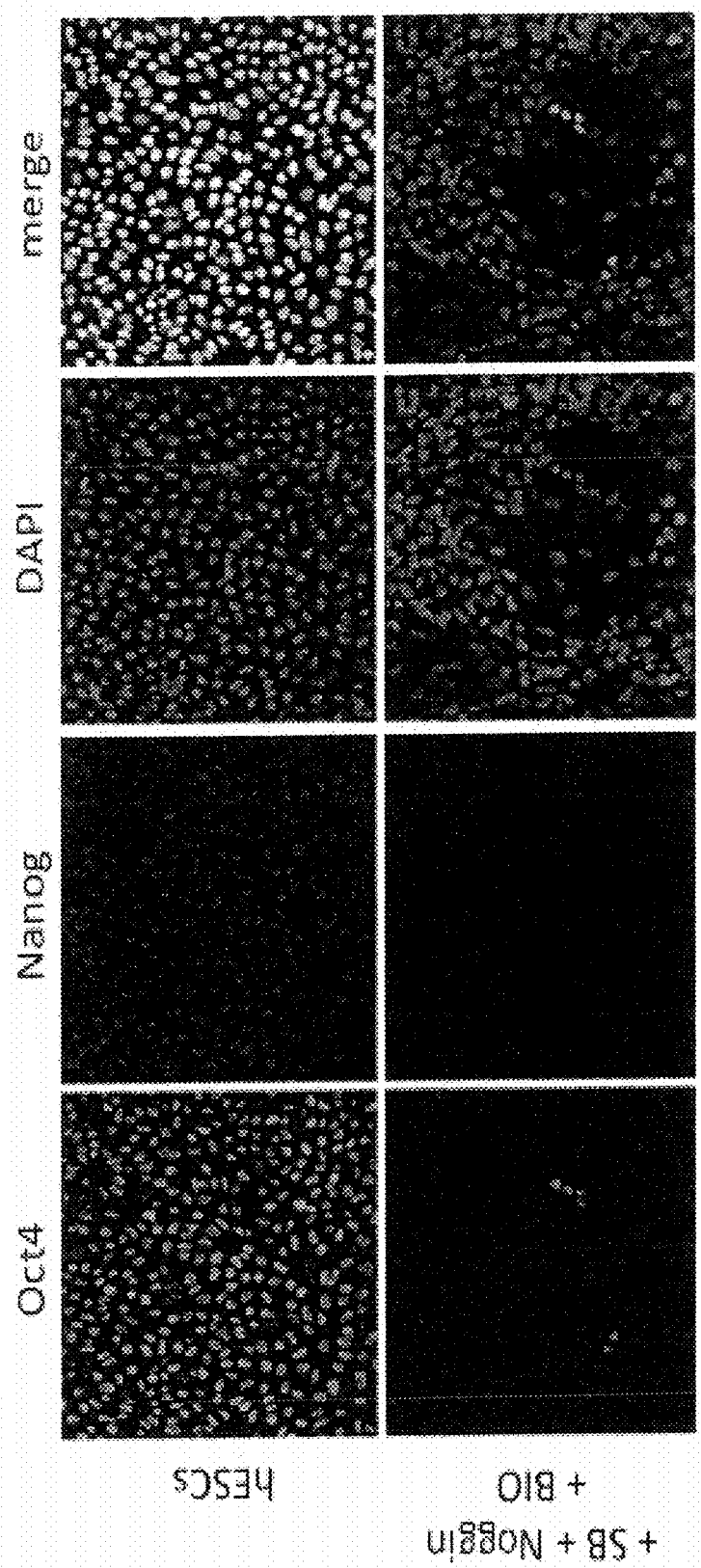
FIGURE 9 (Fig. S3)

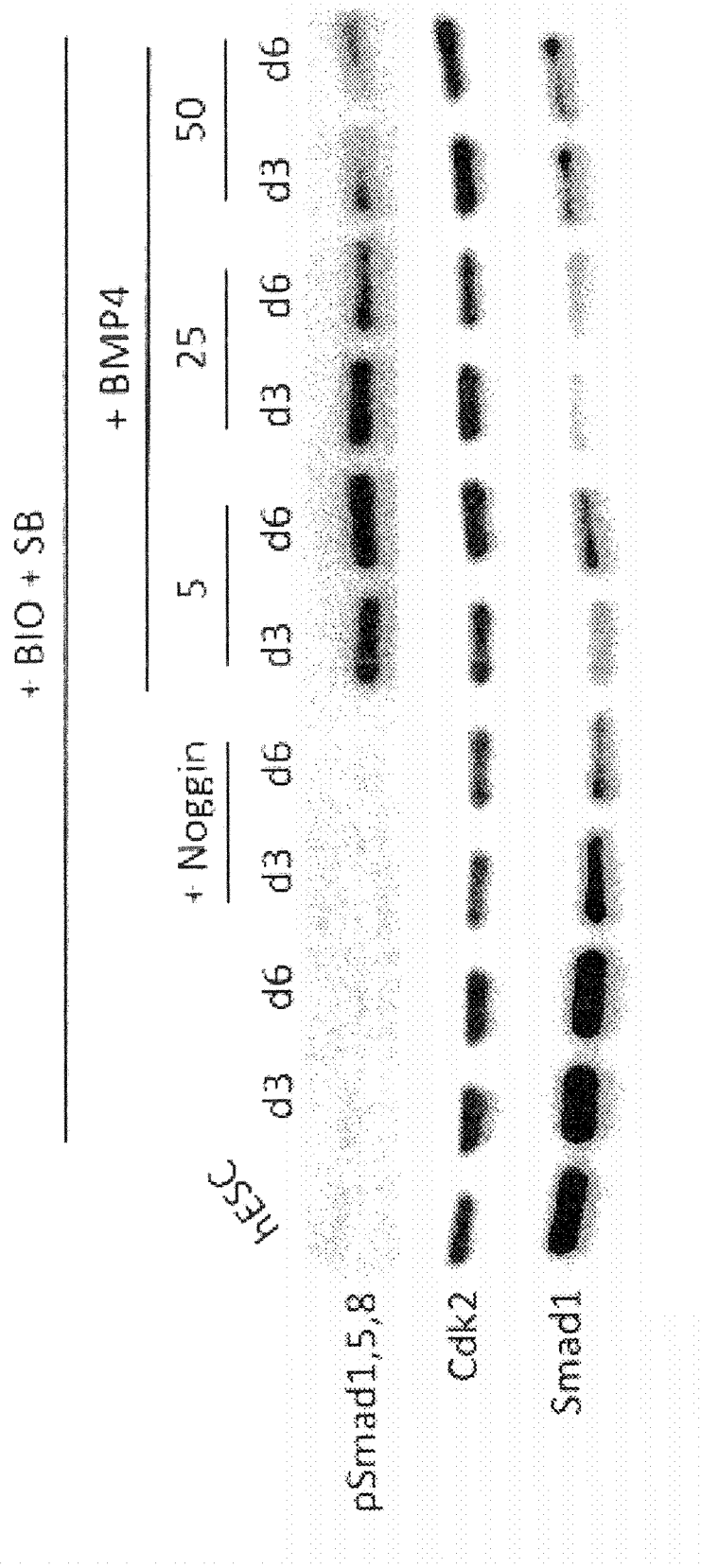
FIGURE 10 (Fig. S4)

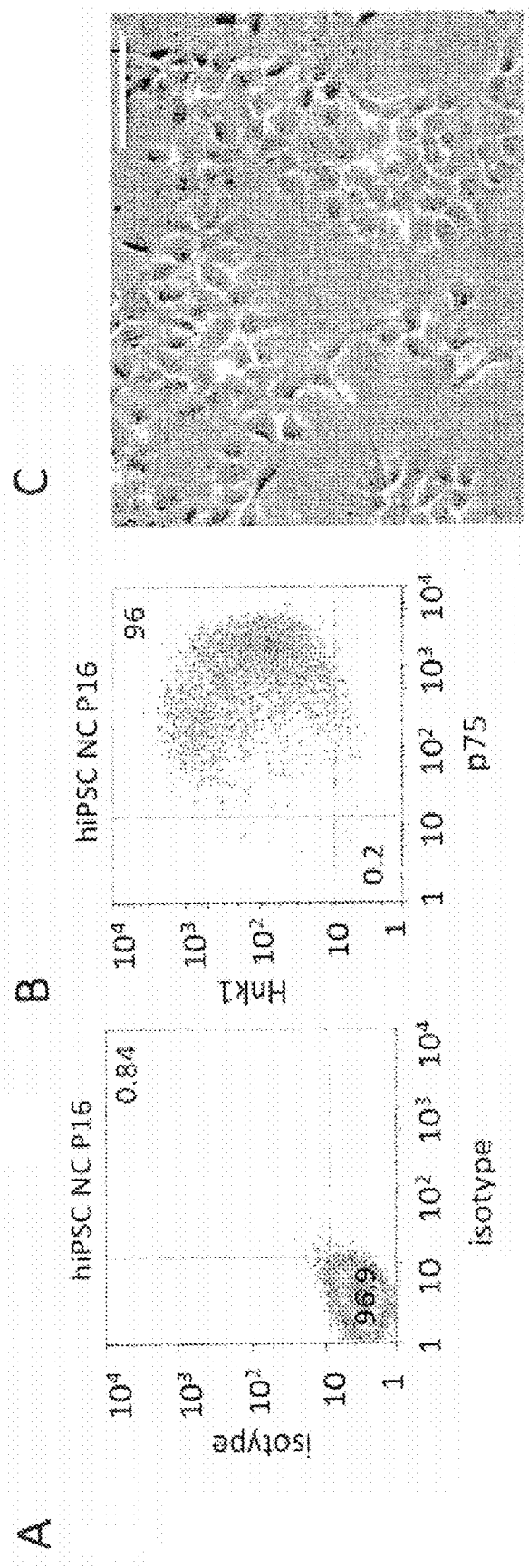
FIGURE 11A, B and C (Fig. S5A, B and C)

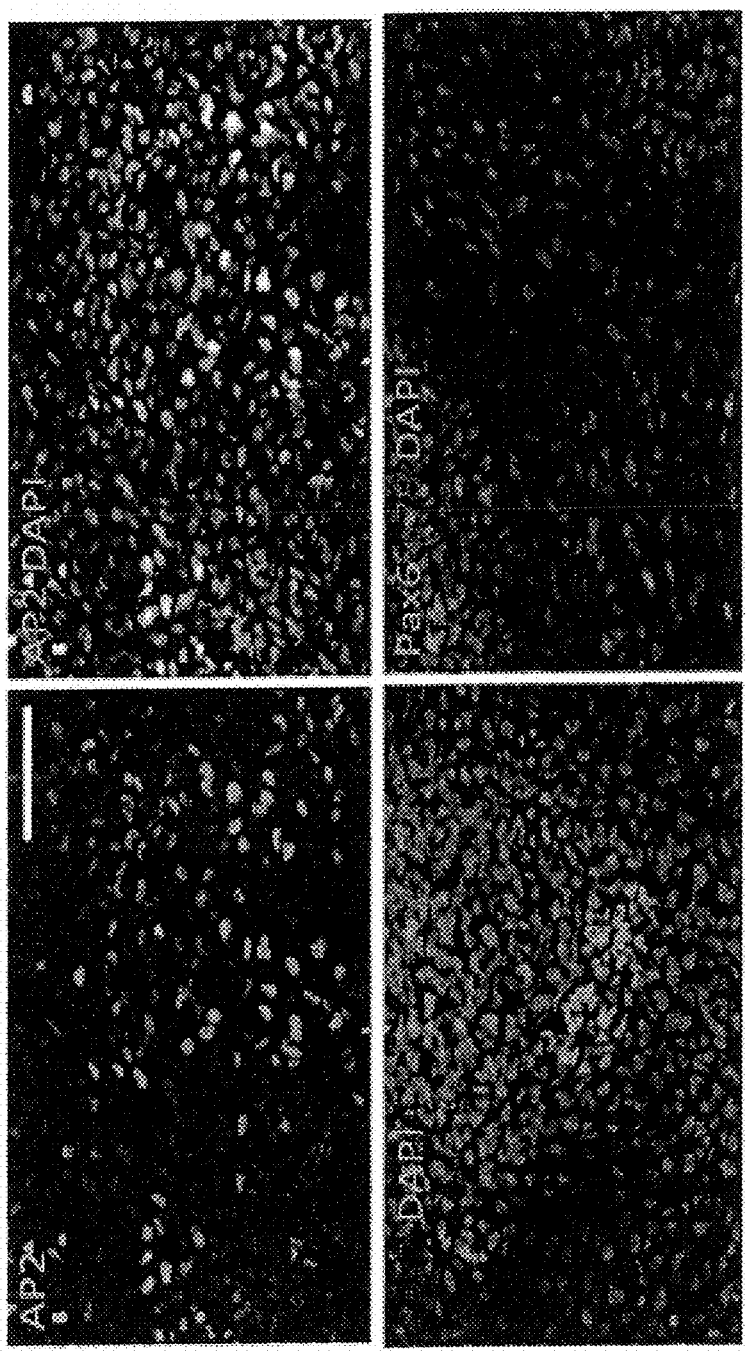
FIGURE 11D (Fig. S5D)

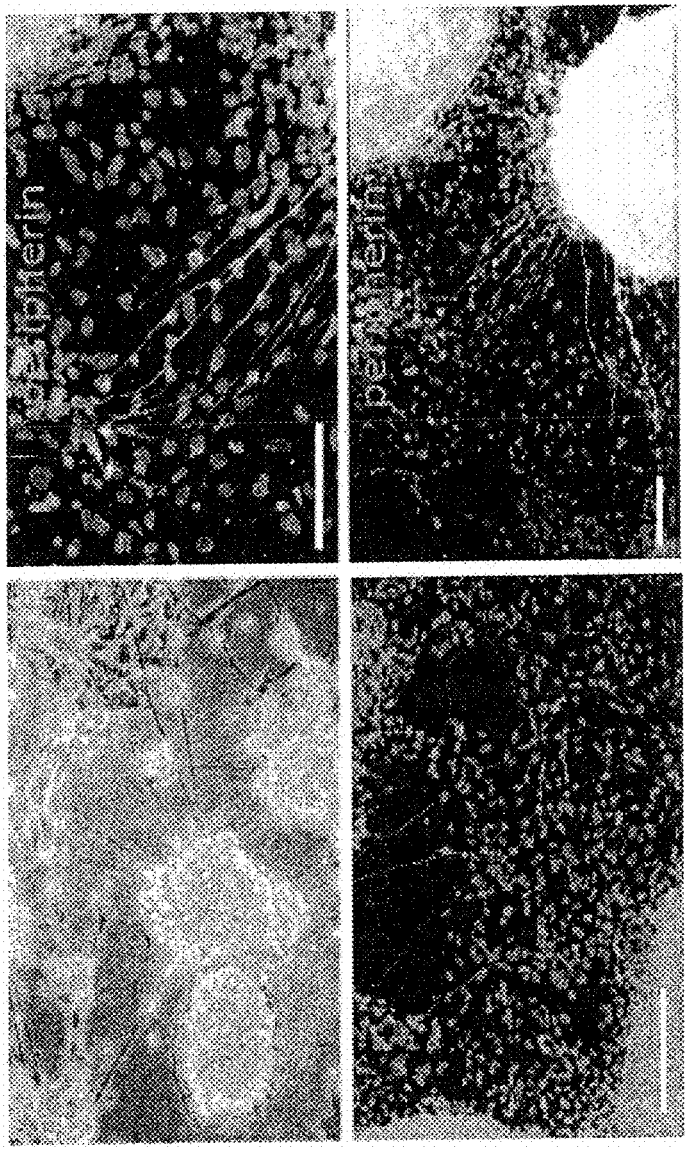
FIGURE 12A (Fig. S6A)

FIGURE 12B (Fig. S6B)
B
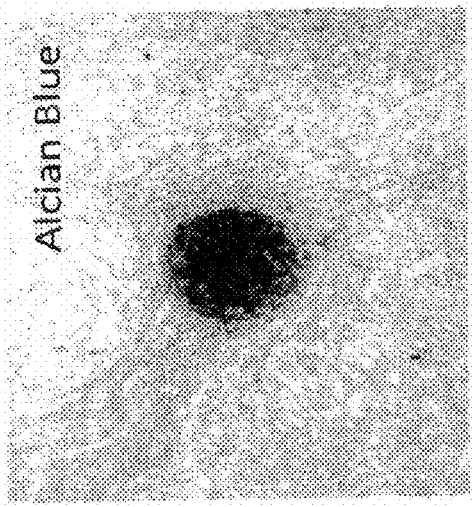
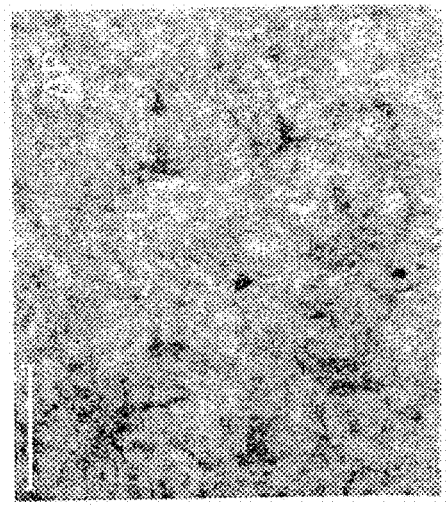
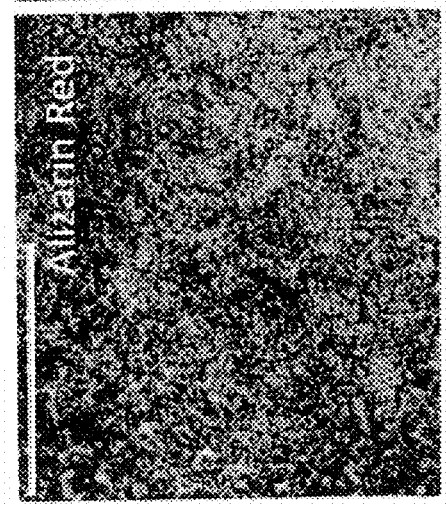

DIFFERENTIATION OF HUMAN PLURIPOTENT STEM CELLS TO MULTIPOTENT NEURAL CREST CELLS

RELATED APPLICATIONS

The present application claims priority from and is a continuation application of U.S. national phase patent application Ser. No. 13/977,387 filed Jun. 28, 2013, which is a 371 application of international patent application number PCT/US2011/065810 filed Dec. 19, 2011, which claims the benefit of priority of provisional application Nos. 61/428,998, filed 31 Dec. 2010; 61/429,344, filed 3 Jan. 2011; 61/429,992, filed 5 Jan. 2011 and 61/548,045, filed 17 Oct. 2011, each of identical title to the present application, and each of said applications being incorporated by reference in its entirety herein.

GRANT SUPPORT

This invention was made with government support under grant number HD049647 awarded by the National Institute of Child Health and grant number GM075334 awarded by the National Institute for General Medical Sciences. The government has certain rights in the invention.

FIELD OF THE INVENTION

The present invention relates to the differentiation of human pluripotent cells, including human pluripotent stems cells (including hiPSCs) to produce a self-renewing multipotent neural crest cell population in a single step method preferably without the requirement of isolating intermediate cells and without appreciable contamination (in certain preferred instances, virtually none) with Pax6+ neural progenitor cells in the population of p75+ Hnk1+ Ap2+ neural crest-like stem cells. The neural crest stem cell population obtained can be clonally amplified and maintained for >25 passages (>100 days) while retaining the capacity to differentiate into peripheral neurons, smooth muscle cells and mesenchymal precursor cells.

BACKGROUND OF THE INVENTION

Neural crest stem cells are a multipotent cell population arising at the neural plate border of neural ectoderm between the neural plate and the non-neural ectoderm during vertebrate embryogenesis (1, 2). As neural crest cells delaminate from the roof plate upon closing of the neural tube, they migrate throughout the body where they contribute to the peripheral nervous system, connective and skeletal cranial tissues, melanocytes and valves of the heart. Specification of ectoderm into neural, neural plate border and epidermal cells is directed by overlapping but distinct combinations of signaling molecules centering around Wnt, BMP and Fgf pathways (3-10). Knowledge of these pathways has been instrumental in establishing conditions for differentiation of human pluripotent cells in culture along a neuroectoderm pathway for the generation of neural progenitor cells (NPCs) and a wide-range of neuronal sub-types (11-13)

Efficient methods for generation of NPCs from human pluripotent cells have recently been made possible by use of specific inhibitors, such as Noggin and SB 431542, that function by blocking BMP and Activin A/Nodal signaling, respectively (12). Simultaneous inhibition of these pathways is sufficient to drive pluripotent cells in culture down the neuroectoderm pathway, generating a population of $Pax6^+$ $Sox1^+$ $Sox2^+$ NPCs that can assemble into neural rosettes as columnar epithelia. When isolated from neural rosettes in culture, NPCs can be amplified due to their self-renewing capacity and further differentiated into a wide range of neural cell types (13, 14). Neural crest cells are typically found interspersed with neural rosettes in such cultures and can only be obtained as a highly enriched cell population by cell sorting techniques (15, 16). Alternative methods for generating neural crest cells from pluripotent cells have been described, but these utilize co-culture on feeder layers (16, 17), are relatively inefficient and also require cell sorting to generate highly enriched populations. These methods all involve complex, multistep procedures that yield relatively low yields of $p75^+$ $Hnk1^+$ neural crest. These issues highlight the limitations of current approaches and consequently, severely limit their utility in scale-up applications for tissue engineering, regenerative medicine and drug screening applications. An efficient, single-step method for generation of neural crest cells from pluripotent cells would therefore represent a significant advancement in understanding their biology and towards their biomedical application.

The heterogeneity of neuroectoderm cultures from which neural crest cells are currently isolated led us to reevaluate the general approach from a cell signaling perspective. While low levels of BMP and Activin A signaling are considered pre-requisites for the generation of NPCs from human embryonic stem cells (hESCs) and human induced pluripotent stem cells (hiPSCs), the potential role of Wnt in specifying neural crest has not been evaluated. This is somewhat surprising considering the well-established role for canonical Wnt signaling in neural crest development in vivo (3-5).

BRIEF DESCRIPTION OF THE INVENTION

The present invention relates to a method for producing a population of p75+ Hnk1+ Ap2+ multipotent neural crest-like cells from human pluripotent cells, preferably human pluripotent stem cells or human induced pluripotent cells in a single step without appreciable contamination with Pax6+ neural progenitor cells in the population of neural crest-like stem cells produced. This approach, which involves differentiation of pluripotent cells through WNT signaling promotion and Activin A/Smad pathway blockade and in addition, in particularly preferred embodiments, the inhibition of bone morphogenic protein (BMP), directs the unexpectedly efficient differentiation of pluripotent cells to the neural crest-like stem cells. The method of the present invention provides for the efficient generation of self-renewing neural crest stem cells that greatly enhance their potential utility in disease modeling and regenerative medicine.

In the present method, human pluripotent cells, preferably human pluripotent stem cells, are exposed to an effective amount of at least one agent which promotes WNT signaling (a WNT signaling promoter which may include a GSK inhibitor as otherwise described herein or a Wnt protein as otherwise described herein) in the presence of an effective amount of at least one agent which inhibits Activin A and similarly acting TGFbeta family members such as TGF beta and nodal (Activin A inhibitor or other suppressor of the Activin A/Nodal, "Activin A inhibitor" or "Activin A/Smad pathway inhibitor") in a cell differentiation medium for an effective amount of time (generally, about 6 to 20 days, about 7 to 18 days, about 8 to 17 days, about 9-15 days, about 10-15 days, about 11 to 15 days, about 12 to 14 days, about 13 to 15 days to produce a population of p75+ Hnk1+ Ap2+ multipotent neural crest-like cells from human pluripotent cells, preferably human pluripotent stem cells in the absence of feeder cells in a single step without appreciable contamination with Pax6+ neural progenitor cells in the population of neural crest-like stem cells produced. In preferred embodiments, contamination of p75+ Hnk1+ Ap2+ neural crest-like stem cells with Pax6+ neural progenitor cells amounts to no more than 10%, no more than 7.5% no more than 5%, no more than 2.5%, no more than 1%, less than 1%, less than 0.5%, less than 0.1%, less than 0.05% and in certain embodiments, undetectable levels of Pax6+ neural progenitor cells.

Pursuant to the present invention, the inventors describe a highly efficient, one-step method for efficient generation of multipotent neural crest-like stem cells (NCSCs) from pluripotent cells such as hESCs and hiPSCs that involves concurrent activation of canonical Wnt signaling under conditions of low global Smad signaling. Cultures arising under these conditions are comprised of highly-enriched NCSCs that are devoid of other contaminating neuroectoderm cell types. NCSCs can be maintained over extended periods in culture while retaining developmental potential for being differentiated into peripheral neurons and mesenchymal progenitor cells which mesenchymal progenitor cells may be further differentiated into osteocytes, chondrocytes and adipocytes. The preferred method of the present invention produces NCSCs directly from human pluripotent cells without the need for co-culture on feeder-layers (the process is preferably feeder cell free) or cell sorting to obtain a highly enriched population (i.e., a population at least about 90% NCSCs). These findings significantly increase the opportunities for use of neural crest cells and their derivatives in tissue engineering, regenerative medicine and drug screening applications.

BRIEF DESCRIPTION OF THE FIGURES

FIG. 7 (FIG. S1). shows WA09 hESCs that were cultured in defined media (Activin A) supplemented with SB 431542 and Noggin for 14 days. Cells were then fixed and stained with antibodies for Pax6, Sox1 and Sox2. DNA was detected by staining with DAPI.

FIG. 8 (FIG. S2) shows a luciferase assay for β-catenin activity in hESCs. (A) BIO treatment of WA09 hESCs activates β-catenin signaling as shown by activation of the Top-Flash luciferase reporter. Data is expressed as the fold-increase in luciferase activity over untreated cells after normalization to the Fop-Flash control. All assays were performed in triplicate and represented as +/−standard deviation. (B) Top-Flash activity in hESCs grown in defined media treated with Wnt3a, Dkk1, Wnt3a and Dkk1 or BIO. Experiments were performed in triplicate and represented as +/−standard deviation.

FIG. 9 (FIG. S3). shows that WA09 hESCs treated with SB 431542, Noggin and BIO down-regulate pluripotency markers Oct4 and Nanog. hESCs were treated with the 3 factors for 12 days then fixed and stained with antibodies for Oct4 and Nanog. DAPI was used to visualize DNA.

FIG. 10 (FIG. S4) shows a western blot analysis for detection of pSmad1,5,8. hESCs were grown for 3-6 days in the presence of BIO and SB 431542 with Noggin alone, BMP4 alone (5-50 ng/ml). Whole cell lysates were then probed with antibodies for Smad1, Cdk2 (load control) or pSmad1,5,8.

FIGS. 11A-C, 11D (FIG. S5). Show hiPSC differentiation to neural crest cells. (A-B) Flow cytometry analysis of hiPSCs treated with BIO and SB431542 in defined media lacking Activin A for 12 days. Flow cytometry analysis was performed using isotype antibody controls (left hand panel) and p75/Hnk1 antibodies (right hand panel). The % of positive cells in bottom left and top right quadrants are indicated. (C) Bright field picture of neural crest cells analyzed in (A). Micron bar, 100 μm. (D) Cells as in (C) were analyzed by immunocytochemistry by probing with antibodies for Ap2, Sox2, p75, Pax6. DNA was visualized by staining with DAPI. Micron bar, 200 μm.

FIGS. 12A, 12B (FIG. S6). Show that hiPSC-derived neural crest cells differentiate into multiple lineages. (A) Generation of peripheral neurons is shown by staining with antibodies for peripherin and β-tubulin. (B) Mesenchymal stem cells generated from hiPSC-derived neural crest can further differentiate into chondrocytes and osteocytes, as shown by staining with Alcian Blue, Alizarin Red and alkaline phosphatase (AP). Micron bar, 200 μm.

DETAILED DESCRIPTION OF THE INVENTION

Figure 1:
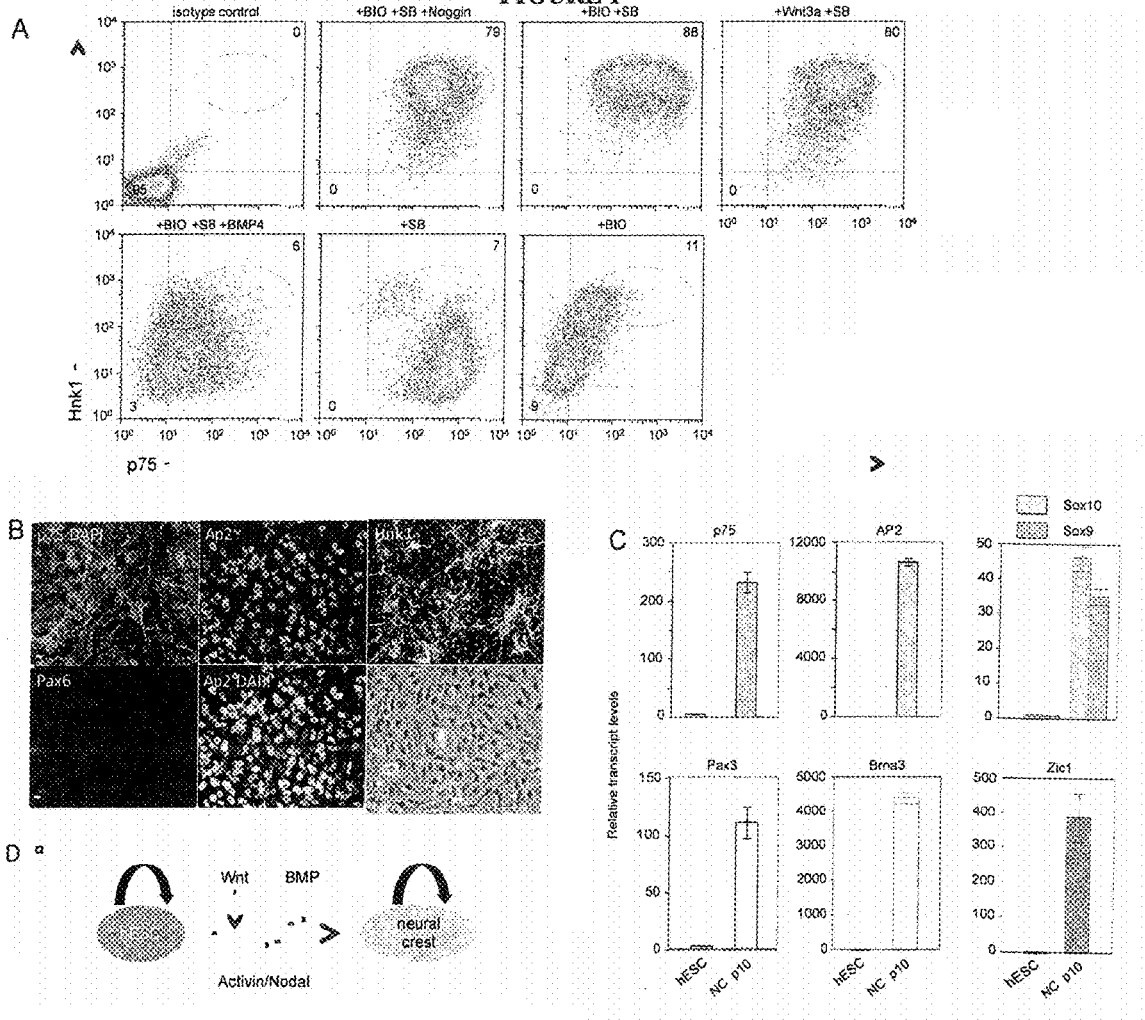
FIG. 1. shows that hESC (WA09) differentiation to neuroprogenitor cells is inhibited by Wnt signaling. (A) Schematic summarizing differentiation of pluripotent cells into neural progenitor cells and neural crest cells together with markers for the two cell types. (B) Treatment of hESCs with SB 431542 (20 µM) and Noggin (500 ng/ml) promotes differentiation into Pax6+ cells but concurrent treatment with BIO suppresses this and generates p75+ Pax6− neural crest-like cells. Scale bar, 100 µm. (C) Flow cytometry showing that Dickkopf (Dkk) decreases the p75bright population in NPC cultures generated by treatment with SB 431542 and Noggin. (D) Real-time PCR data for Ap2 and Pax6 from p75dim or p75bright sorted cells (from C).

The following terms shall be used to describe the present invention.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized.

The present invention may be understood more readily by reference to the following detailed description of the preferred embodiments of the invention and the Examples included herein. However, before the present compositions and methods are disclosed and described, it is to be understood that this invention is not limited to specific conditions, or specific methods, etc., as such may, of course, vary, and the numerous modifications and variations therein will be apparent to those skilled in the art.

Standard techniques for growing cells, separating cells, and where relevant, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth. Enzymol. 68; Wu et al., (Eds.) 1983 Meth. Enzymol. 100 and 101; Grossman and Moldave (Eds.) 1980 Meth. Enzymol. 65; Miller (ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

The term "primate Pluripotent Stem Cells", also "primate Pluripotent cells" of which "human Embryonic Stem Cells" or hESCs are a subset and preferred for use in the present invention, are derived from pre-embryonic, embryonic, or fetal tissue at any time after fertilization, and have the characteristic of being capable under appropriate conditions of producing progeny of several different cell types that are derivatives of all of the three germinal layers (endoderm, mesoderm and ectoderm), according to a standard art-accepted test, such as the ability to form teratomas in 8-12 week old SCID mice. The term includes both established lines of stem cells of various kinds, and cells obtained from primary tissue that are pluripotent in the manner described.

Included in the definition of pluripotent cells or pPS cells (pPSCs) are embryonic cells of various types, especially including human embryonic stem cells (hESCs), described by Thomson et al. (Science 282: 1145, 1998); as well as embryonic stem cells from other primates, such as Rhesus stem cells (Thomson et al., Proc. Natl Acad. Sci. USA 92: 7844, 1995). Other types of pluripotent cells are also included in the term. Human Pluripotent Stem Cells include stem cells which may be obtained from human umbilical cord or placental blood as well as human placental tissue. Any cells of primate origin that are capable of producing progeny that are derivatives of all three germinal layers are included, regardless of whether they were derived from embryonic tissue, fetal, or other sources. The pPS ce+lls are preferably not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells, clearly distinguishing them from differentiated cells of embryo or adult origin. Undifferentiated pPS cells are easily recognized by those skilled in the art, and typically appear in the two dimensions of a microscopic view in colonies of cells with high nuclear/cytoplasmic ratios and prominent nucleoli. It is understood that colonies of undifferentiated cells in the population will often be surrounded by neighboring cells that are differentiated.

Pluripotent stem cells may express one or more of the stage-specific embryonic antigens (SSEA) 3 and 4, and markers detectable using antibodies designated Tra-1-60 and Tra-1-81 (Thomson et al., Science 282:1145, 1998). Differentiation of pluripotent stem cells in vitro results in the loss of SSEA-4, Tra-1-60, and Tra-1-81 expression (if present) and increased expression of SSEA-1. Undifferentiated pluripotent stem cells typically have alkaline phosphatase activity, which can be detected by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another desirable phenotype of propagated pluripotent stem cells is a potential to differentiate into cells of all three germinal layers: endoderm, mesoderm, and ectoderm tissues. Pluripotency of pluripotent stem cells can be confirmed, for example, by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. Non-limiting examples are established lines of human embryonic stem cells or human embryonic germ cells, such as, for example the human embryonic stem cell lines WA01, WA07, and WA099 (WiCell). Also contemplated is use of the compositions of this disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BG01v (BresaGen, Athens, Ga.), as well as normal human embryonic stem cell lines such as WA01, WA07, WA09 (WiCell) and BG01, BG02 (BresaGen, Athens, Ga.).

Epiblast stem cells (EpiScs) and induced pluripotent stem cells (iPSCs) including human induced pluripotent stems cells (hiPSCs) fall within the broad definition of pluripotent cells hereunder and in concept, the technology described in the present application could apply to these and other pluripotent cell types (ie, primate pluripotent cells) as set forth above. EpiScs are isolated from early post-implantation stage embryos. They express Oct4 and are pluripotent. See, Tesar et al, *Nature, Vol* 448, p. 196 12 Jul. 2007. iPS cells are made by dedifferentiating adult somatic cells back to a pluripotent state by retroviral transduction of four genes (c-myc, Klf4, Sox2, Oct4). See, Takahashi and Yamanaka, Cell 126, 663-676, Aug. 25, 2006.

Human embryonic stem cells may be prepared by methods which are described in the present invention as well as in the art as described for example, by Thomson et al. (U.S. Pat. No. 5,843,780; *Science* 282:1145, 1998; *Curr. Top. Dev. Biol.* 38:133 ff., 1998; *Proc. Natl. Acad. Sci. U.S.A.* 92:7844, 1995).

The use of human pluripotent cells in the present invention is preferred.

The term "embryonic stem cell" refers to pluripotent cells, preferably of primates, including humans, which are isolated from the blastocyst stage embryo. Human embryonic stem cell refers to a stem cell from a human and are preferably used in aspects of the present invention which relate to human therapy or diagnosis. The following phenotypic markers are expressed by human embryonic stem cells:

SSEA-3, SSEA-4, TRA-1-60, TRA-1-81, CD9, alkaline phosphatase, Oct 4, Nanog, Rex 1, Sox2 and TERT. See Ginis, et al., *Dev. Biol*, 269(2), 360-380 (2004); Draper, et al., *J. Anat.*, 200 (Pt. 3), 249-258, (2002); Carpenter, et al., *Cloning Stem Cells*, 5(1), 79-88 (2003); Cooper, et al., *J. Anat.*, 200 (Pt. 3), 259-265 (2002); Oka, et al., *Mol. Biol. Cell*, 13(4), 1274-81 (2002); and Carpenter, et al., *Dev. Dyn.*, 229(2), 243-258 (2004). While any primate pluripotent stem cells (pPSCs), including especially human embryonic stem cells can be used in the present methods to produce neural crest stem cells according to the present invention, preferred pPSCs for use in the present invention include human embryonic stem cells, including those from the cell lines BG01 and BG02, as well as numerous other available stem cell lines.

Alternatively, induced pluripotent cells (iPSCs), especially human induced pluripotent cells (hiPSCs) are preferred for use in the present invention.

The term "differentiation" is used to describe a process wherein an unspecialized ("uncommitted") or less specialized cell (a pluripotent stem cell as otherwise disclosed herein, preferably, a human embryonic stem cell) acquires the features of a more specialized cell, in this case, p75+ Hnk1+ Ap2+ neural crest-like stem cells. A differentiated or differentiation-induced cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and what cells it can give rise to. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

The term "appreciable" within the context of contamination of p75+ Hnk1+ Ap2+ neural crest-like stem cells with Pax6+ neural progenitor cells means an amount which is less than about 10-15%, and preferably less than about 5-10% of the total amount or number of p75+ Hnk1+ Ap2+ neural crest-like stem cells which are produced using methods according to the present invention. In preferred embodiments of the present invention, contamination of p75+ Hnk1+ Ap2+ neural crest-like stem cells with Pax6+ neural progenitor cells amounts to no more than 10%, no more than 7.5% no more than 5%, no more than 2.5%, no more than 1%, less than 1%, less than 0.5%, less than 0.1%, less than 0.05% and in certain embodiments, undetectable levels of Pax6+ neural progenitor cells.

As used herein, the terms "differentiation medium", "cell differentiation medium", "culture media", "basal cell medium", "basal cell media" or "basal media" or "stabilizing medium" are used synonymously to describe a cellular growth medium in which (depending upon the additional components used) the pluripotent stem cells, preferably hESCs and/or neural crest cells as otherwise described herein) are produced, grown/cultured or alternatively and more particularly, differentiated into more mature cells. Differentiation media are well known in the art and consist essentially of at least a minimum essential medium plus one or more optional components (in the case of the formation of neural crest cells, a defined media as known in the art, without Activin A in combination with the other components is preferably used as is disclosed herein). See, Lee, et al., (2010) Derivation of neural crest cells from human pluripotent stem cells. *Nat Protoc* 5(4):688-701, relevant portions of which are incorporated by reference herein. Other media, well known in the art, may also be used.

Differentiation media for producing peripheral neurons include preferably neurotrophic factors) in effective amounts especially including for example, Heregulin β (at about 1-25 ng/ml, preferably about 10 ng/ml), BDNF (brain derived neurotrophic factor, about 5 to 25 ng/ml, preferably about 10 ng/ml), GDNF (glial cell line derived neutrophic factor, about 5-25 ng/ml, preferably about 10 ng/ml), neurotophin-3 (about 5-25 ng/ml, preferably about 10 ng/ml), NGF (nerve growth factor, about 5-25 ng/ml, preferably about 10 ng/ml), ascorbic acid (50-500 μM, preferably about 200 μM) and dbcAMP (Dibutyryl cyclic adenosine monophosphate, about 0.1 to about 1 mM, preferably about 0.5 mM), other optional components may include such components as LR-Igf (about 50-500 ng./ml, and other optional components such as growth factors, including fibroblast growth factor (e.g., bFGF at about 1-20 ng/ml, about 5-10 ng/ml, about 8 ng/ml), glucose, non-essential amino acids, salts (including trace elements), glutamine, insulin (where indicated and not excluded), Activin A (excluded in preferred embodiments according to the present invention), transferrin, beta mercaptoethanol, and other agents well known in the art and as otherwise described herein. Preferred media includes Bovine Serum media (BS media) such as a basal cell media which may contain between 1% and 20% (preferably, about 2-10%) fetal calf serum, or for chemically defined medium (preferred) an absence of fetal calf serum and KSR, but including bovine serum albumin (about 1-5%, preferably about 2%). Differentiation medium, which is used is defined and preferably contains fetal bovine serum. Preferred differentiation media is that which is described in the examples which follow.

In preferred embodiments wherein p75+ Hnk1+ Ap2+ neural crest-like stem cells are produced, the preferred media is a basal media or other chemically defined media as otherwise described which enhances Wnt signaling (using, for example, a GSK inhibitor or a Wnt protein as otherwise described herein) and inhibits the Activin A/Smad pathway using an Activin A inhibitor as otherwise described herein in an effective amount. Optionally, and in certain cases, preferably an effective amount of a BMP inhibitor as otherwise described herein is also included in the media. In the present invention, during differentiation, inhibitors of Wnt signaling and promoters of Activin A and other promoters of the Activin A/Smad pathway such as Activin A, as well as BMP pathway promoters, are preferably excluded from the differentiation media.

Other agents which optionally may be added to differentiation medium (depending upon the end product to be produced with the differentiation medium) include, for example, nicotinamide, members of TGF-β family, including TGF-β1, 2, and 3, Activin A, nodal, serum albumin, members of the fibroblast growth factor family, platelet-derived growth factor-AA, and -BB, platelet rich plasma, insulin growth factor (IGF-I, II), growth differentiation factor (GDF-5, -6, -8, -10, 11), glucagon like peptide-I and II (GLP-I and II), GLP-1 and GLP-2 mimetobody, Exendin-4, parathyroid hormone, insulin, progesterone, aprotinin, hydrocortisone, ethanolamine, epidermal growth factor (EGF), gastrin I and II, copper chelators such as, for example, triethylene pentamine, forskolin, Na-Butyrate, betacellulin, ITS, noggin, neurite growth factor, nodal, valporic acid, trichostatin A, sodium butyrate, hepatocyte growth factor (HGF), sphingosine-1, VEGF, MG132 (EMD, CA), N2 and B27 supplements (Gibco, CA), steroid alkaloid such as, for example, cyclopamine (EMD, CA), keratinocyte growth factor (KGF), Dickkopf protein family, bovine pituitary extract, islet neogenesis-associated protein (INGAP), Indian hedgehog, sonic hedgehog, proteasome inhibitors, notch pathway inhibitors, sonic hedgehog inhibitors, or combinations thereof, among a number of other components. Each of these components, when included as optional components, are included in effective amounts.

By way of further example, suitable media may be made from the following components, such as, for example, Dulbecco's modified Eagle's medium (DMEM), Gibco #11965-092; Knockout Dulbecco's modified Eagle's medium (KO DMEM), Gibco #10829-018; Ham's F12/50% DMEM basal medium; 200 mM L-glutamine, Gibco #15039-027; non-essential amino acid solution, Gibco 11140-050; β-mercaptoethanol, Sigma #M7522; human recombinant basic fibroblast growth factor (bFGF), Gibco #13256-029. Preferred embodiments of media used in the present invention are as otherwise described herein.

A particularly preferred differentiation medium for growing/culturing pPSCs (especially, hESCs) and for differentiating cells in the present invention is defined media without Activin A (for neural crest differentiation) and DMEM/F12 (50:50) for peripheral neuron differentiation from multipotent neural crest cells which contains about 2% proalbumin (albumin; Millipore/Serologicals), 1× Pen/Strep, 1×NEAA, 1× Trace Elements A, B, C (Mediatech), Ascorbic Acid (10-100 ng/ml, about 25-65 ng/ml, about 50 ng/ml), about 0.1 mM (0.025-0.5 mM) β-Mercaptoethanol (Gibco), about 2-10 ng/ml, about 5-9 ng/ml, about 8 ng/ml bFGF (Sigma), 200 ng/ml (5-500 ng/ml) LR-IGF (referred to as IGF-I; JRH Biosciences), and 10 ng/ml (about 1-20 ng/ml or more) Heregulin. In certain preferred embodiments in differentiation medium according to the present invention Activin A is excluded. In other instances, depending upon the end product and the type of medium used (maintence medium, etc.) Activin A is including at about 10 ng/ml (i.e., from about 1 ng/ml to no more than about 20 ng/ml).

Differentiation media useful in the present invention are commercially available and can be supplemented with commercially available components, available from Invitrogen Corp. (GIBCO), Cell Applications, Inc. and Biological Industries, Beth HaEmek, Israel, among numerous other commercial sources, including Calbiochem. In preferred embodiments at least one differentiation agent such as fibroblast growth factor (FGF), LR-IGF (an analogue of insulin-like growth factor) and Heregulin (preferably all three in effective amounts) is added to the cell media in which a stem cell is cultured and differentiated into a neural crest cell, as otherwise described herein. In preferred embodiments, the cell differentiation media comprises at least one promoter of Wnt Signaling such as a GSK inhibitor or Wnt protein as otherwise described herein alone, or optionally in combination with an inhibitor of Activin A/Smad pathway and further optionally in combination with a BMP inhibitor as otherwise described herein. BMP inhibitors such as noggin, chordin, follistatin, sclerostin, gremlin, dorsomorphorin (dorsomorphin dihydrochloride), connective tissue growth factor (CTGF), among others, may also be used in conjunction with Activin A inhibitors and GSK inhibitors/Wnt proteins for the purpose of differentiation. A combination of these agents may be preferred. Each of these components is used in any effective amount as otherwise described herein. One of ordinary skill in the art will be able to readily modify the cell media to produce any one or more of the target cells pursuant to the present invention.

Cell differentiation medium is essentially synonymous with basal cell medium but is used within the context of a differentiation process and includes cell differentiation agents to differentiate cells into other cells, in the preferred methods, p75+ Hnk1+ Ap2+ neural crest-like stem cells. Stabilizing medium is a basal cell medium which is used either before or after a differentiation step in order to stabilize a cell line for further use. Culture media is essentially the same as stabilizing medium, but refers to media in which a pluripotent or other cell line is grown or cultured prior to differentiation. In general, as used herein, cell differentiation medium and stabilizing medium may include essentially similar components of a basal cell medium, but are used within different contexts and may include slightly different components in order to effect the intended result of the use of the medium.

In the present invention, pluripotent stem cells also may be cultured on a layer of feeder cells that support the pluripotent stem cells in various ways which are described in the art, but in preferred embodiments the stem cells are differentiated in a feeder cell free environment. Alternatively, pluripotent stem cells are cultured in a culture system that is essentially free of feeder cells, but nonetheless supports proliferation of pluripotent stem cells without undergoing substantial differentiation. The growth of pluripotent stem cells in feeder-free culture without differentiation is preferred and is supported using a medium conditioned by culturing previously with another cell type. Alternatively, the growth of pluripotent stem cells in feeder-free culture without differentiation is supported using a chemically defined medium. These approaches are well known in the art. In preferred aspects of the present invention, the cells are grown in feeder cell free medium.

The term "GSK inhibitor" is used to describe a compound which inhibits GSK (especially GSK3, including GSK3α or GSK3β), and compounds which are GSK inhibitors are useful in promoting the WNT pathway pursuant to the present invention. Thus, WNT pathway promoters which may be used in the present invention include GSK inhibitors as otherwise described herein. Examples of preferred GSK inhibitors for use in the present invention include one or more of the following, all available from Calbiochem:

BIO (2'Z,3'E)-6-Bromoindirubin-3'-oxime (GSK3 Inhibitor IX);
BIO-Acetoxime (2'Z,3'E)-6-Bromoindirubin-3'-acetoxime (GSK3 Inhibitor X);
(5-Methyl-1H-pyrazol-3-yl)-(2-phenylquinazolin-4-yl) amine (GSK3-Inhibitor XIII);
Pyridocarbazole-cyclopenadienylruthenium complex (GSK3 Inhibitor XV);
TDZD-8 4-Benzyl-2-methyl-1,2,4-thiadiazolidine-3,5-dione (GSK3β Inhibitor I);
2-Thio(3-iodobenzyl)-5-(1-pyridyl)-[1,3,4]-oxadiazole (GSK3β Inhibitor II);
OTDZT 2,4-Dibenzyl-5-oxothiadiazolidine-3-thione (GSK3β Inhibitor III);
α-4-Dibromoacetophenone (GSK3β Inhibitor VII);
AR-A014418 N-(4-Methoxybenzyl)-N'-(5-nitro-1,3-thiazol-2-yl)urea (GSK-3β Inhibitor VIII);
3-(1-(3-Hydroxypropyl)-1H-pyrrolo[2,3-b]pyridin-3-yl]-4-pyrazin-2-yl-pyrrole-2,5-dione (GSK-3β Inhibitor XI);
TWS119 pyrrolopyrimidine compound (GSK3β Inhibitor XII);
L803 H-KEAPPAPPQSpP-NH$_2$ or its Myristoylated form (GSK3β Inhibitor XIII); and
2-Chloro-1-(4,5-dibromo-thiophen-2-yl)-ethanone (GSK3β Inhibitor VI).

A preferred GSK inhibitor for use as a WNT pathway promoter in the present invention is BIO, described above, which may be used alone or in combination with another GSK inhibitor. Other GSK inhibitors described may also be used, either alone or in combination with another GSK inhibitor and/or a Wnt protein, as described below, in further combination with an Activin A/Smad inhibitor (e.g., SB431542 as described below) and optionally, a BMP inhibitor.

In addition, numerous wingless proteins or Wnt proteins function similar to GSK inhibitors and in particular, GSK inhibitors according to the present invention. They are therefore subsumed under the term Wnt signaling promoter. Exemplary Wnt proteins which may be used in the present invention include one or more of Wnt1, Wnt2, Wnt3, Wnt3a, Wnt4, Wnt10, Wnt 14, Wnt14b, Wnt15, and Wnt16, among other Wnt proteins. The use of Wnt3a is preferred.

Preferred Wnt signaling promoters include GSK inhibitors such as BIO (GSK-3 IX) and Wnt3a, used alone or in combination. In certain preferred aspects of the invention the Wnt signaling promoter is used in combination with the Activin A/Smad pathway inhibitor and optionally, further in combination with a BMP inhibitor as otherwise described herein. BIO and/or Wnt3a may be used alone, preferably in combination with the Activin A/Smad pathway inhibitor, in particular, SB431542 and further preferably, in combination with a BMP inhibitor, for example noggin, among others as otherwise disclosed herein.

The term "Activin A inhibitor" or "Activin A/Smad pathway inhibitor" is used generically to describe compounds or components which are added to a differentiation medium to inhibit the effects of Activin A/Smad pathway (thus inhibiting Activin A and other molecules which can signal through Smad such as TGFbeta, Nodal, and other compounds) in the differentiation process (Smad pathway inhibitor) and when used, produce neural crest-like stem cells from human pluripotent cells, including hESCs in high yield. In order to produce a population of p75+ Hnk1+ Ap2+ neural crest-like stem cells from hESCs in high yield according to the present invention, the differentiation agent comprises an effective amount of a GSK inhibitor and/or Wnt protein (preferably, a GSK3 inhibitor, such as BIO or other GSK3 inhibitor or a Wnt protein such as Wnt3a) and an Activin A inhibitor and optionally, a BMP inhibitor as otherwise described herein in a cell differentiation medium.

Exemplary Activin A inhibitors for use in the present invention include, for example, SB-431542 (Sigma), follistatin (which also may be considered a BMP inhibitor in the present invention), follistatin gene related protein (FGRP, available from R and D Systems), BMP and Activin Membrane Bound Inhibitor (BAMBI), anti-BAMBI (monoclonal antibody), Smad7 (Mothers Against Decapentaplegic Homolog 7) and TGF RI inhibitor (Calbiochem), among others. Activin A inhibitors are used in the present invention in effective amounts, generally within the range of about 0.001 to about 100 µM or more, about 0.05 to about 75 µM, about 0.1 to about 50 µM, about 0.25 to about 35 µM, about 0.5 to about 25 µM. The use of SB 431542 is preferred and is used preferably in combination with BIO and/or Wnt3a and an optional BMP inhibitor such as noggin.

The term "BMP inhibitor" is used to describe a compound which inhibits bone morphogenic protein signaling in a cell and facilitates the differentiation in effective amounts in combination with WNT Signaling Promoter and an Activin A/Smad Pathway Inhibitor. Exemplary BMP inhibitors for use in the present invention include, for example, at least one inhibitor selected from the group consisting of noggin, chordin, follistatin (which also may be used as an Activin A/Smad pathway inhibitor), sclerostin, gremlin, dorsomorphin (e.g. dorsomorphin dihydrochloride or Stemolecule™) and connective tissue growth factor (CTGF), among others. In the present invention, the addition of factors that block BMP signaling (i.e., a BMP inhibitor) is not required. But it is shown that BMP does inhibit neural cress formation if added. This is explained by low BMP signaling in the media which is presented in the examples (see Appendix A). Thus, while not required, the inclusion of a BMP inhibitor in effective amounts represents a preferred embodiment of the present invention in a number of instances.

As used herein, the term "activate" refers to an increase in expression of a marker such as p75, Hnk.1, Ap2 (in the case of the preferred neural crest-like stem cells) or Pax6 (in the case of neural progenitor cells) or an upregulation of the activity of p75, Hnk1, Ap2 or Pax6.

As used herein when referring to a cell, cell line, cell culture or population of cells, the term "isolated" refers to being substantially separated from the natural source of the cells such that the cell, cell line, cell culture, or population of cells are capable of being cultured in vitro. In addition, the term "isolating" is used to refer to the physical selection of one or more cells out of a group of two or more cells, wherein the cells are selected based on cell morphology and/or the expression of various markers.

As used herein, the term "express" refers to the transcription of a polynucleotide or translation of a polypeptide (including a marker) in a cell, such that levels of the molecule are measurably higher in or on a cell that expresses the molecule than they are in a cell that does not express the molecule. Methods to measure the expression of a molecule are well known to those of ordinary skill in the art, and include without limitation, Northern blotting, RT-PCT, in situ hybridization, Western blotting, and immunostaining.

As used herein, the term "Markers" describes nucleic acid or polypeptide molecules that are differentially expressed in a cell of interest. In this context, differential expression means an increased level for a positive marker and a decreased level for a negative marker. The detectable level of the marker nucleic acid or polypeptide is sufficiently higher or lower in the cells of interest compared to other cells, such that the cell of interest can be identified and distinguished from other cells using any of a variety of methods known in the art.

As used herein, the term "contacting" (i.e., contacting a cell with a compound) is intended to include incubating the compound and the cell together in vitro (e.g., adding the compound to cells in culture). The term "contacting" is not intended to include the in vivo exposure of cells to a differentiation agent that may occur naturally in a subject (i.e., exposure that may occur as a result of a natural physiological process). The step of contacting the cell with differentiation medium and a Wnt signaling promoter (e.g. a GSK inhibitor such as BIO or Wnt protein such as Wnt3a or as otherwise described herein) and Activin A/Smad pathway inhibitor (e.g. SB431542 or as otherwise described herein) and optionally, a BMP inhibitor as otherwise disclosed herein can be conducted in any suitable manner. For example, the cells may be treated in adherent culture as an adherent layer, as embryoid bodies or in suspension culture, although the use of adherent layers may be preferred because they provide an efficient differentiation process oftentimes providing differentiation to a target cell population of 90% or more. It is understood that the cells contacted with the differentiation agent may be further treated with other cell differentiation environments to stabilize the cells, or to differentiate the cells further, for example to produce neural progenitor cells or other cells.

In the case of producing neural-like crest cells from pluripotent stem cells, in particular, human embryonic stem cells, the cells are differentiated in a medium as otherwise disclosed herein comprising effective amounts of a Wnt signaling promoter (GSK inhibitor and/or Wnt protein as otherwise described herein in combination with an effective amount of an Activin A/Smad pathway inhibitor as otherwise disclosed herein and optionally, an effective amount of a BMP inhibitor. The use of BIO and/or Wnt3a in combination with SB431542 is preferred, as is the inclusion of a BMP inhibitor as otherwise described herein, in particular noggin. Components which inhibit Wnt signaling and/or promote the Activin A/Smad pathway (e.g. Activin A) are generally excluded or reduced in amount to have little or no impact on the result of the differentiation process. In a number of instances, the inclusion of a BMP inhibitor is not required (depending upon whether the differentiation medium enhances BMP activity, although in certain preferred instances, where it is desired to inhibit BMP signaling, a BMP inhibitor is also included in effective amounts.

As used herein, the term "differentiation agent" refers to any compound or molecule that induces a cell such as hESC's, neural-like crest cells, neural progenitor cells, etc. to partially or terminally differentiate. While the differentiation agent may be as described below, the term is not limited thereto. The term "differentiation agent" as used herein includes within its scope a natural or synthetic molecule or molecules which exhibit(s) similar biological activity.

The term "effective" is used to describe an amount of a component, compound or compositions which is used or is included in context in an amount and for a period sufficient to produce an intended effect. By way of example, an effective amount of a differentiation agent is that amount which, in combination with other components, in a differentiation medium will produce the differentiated cells desired.

The term "consisting essentially of" is used to describe media, in particular differentiation media which is used to differentiate pluripotent stem cells, especially human pluripotent stem cells such as human embryonic stem cells to neural-like crest cells which contains those components or elements which are useful for effecting the intended differentiation result ("the basic and novel characteristics of the present invention") and limits or eliminates those elements which detract from providing the intended result of the present invention which is directed to a method for differentiating pluripotent cells to neural-like crest cells in high yield without appreciable contamination with Pax6+ neural progenitor cells.

Specific examples which are directed to the present invention are presented hereinbelow. The examples are not to be construed as limiting the scope of the present invention.

Examples

Materials and Methods
Stem Cell Culture.

WA09 (WiCell), RUES1, RUES2 (Dr. A. Brivanlou, Rockefeller University) hESCs and the hiPSC lines Fib2-iPS4 and Fib2-iPS5 (Dr. George Daley, Children's Hospital Boston) were cultured on Geltrex (Invitrogen)-coated plates in chemically defined media containing Hereguling β (10 ng/ml), Activin A (10 ng/ml), LR-Igf (200 ng/ml) and Fgf2 (8 ng/ml) as described previously (25).

Neuroprogenitor Cell, Neural Crest and Mesenchymal Cell Differentiation.

NPC differentiation was performed as described (18). Briefly, cells were plated on Geltrex-coated plates in defined media without Activin A, supplemented with 20 μM SB 431542 (Tocris) and 500 ng/ml Noggin (R&D systems) for 11 days with or without 2 μM of (2'Z,3'E)-6-Bromoindirubin-3'-oxime (BIO) (GSK3 Inhibitor IX, Calbiochem), or 15 ng/ml Dickkopf (R&D Systems). For direct neural crest differentiation, cells were plated at a density of $1 \times 10^5$ cells/cm$^2$ in defined media lacking Activin A, supplemented with 2 μM BIO and 20 μM SB 431542 (SB media). Media was replaced every day. Additional experiments were performed by adding 25 ng/ml Wnt3a, 500 ng/ml Noggin or 5-50 ng/ml of BMP4 (R&D Systems) to SB media. For peripheral neuron differentiation, neural crest cells were plated in poly-L-ornithine/laminin or Geltrex-coated 4-well chamber slides. The following day, SB media was switched to DMEM/F12 N2 supplemented media with BDNF (10 ng/ml), GDNF (10 ng/ml), NGF (10 ng/ml), neurotrophin-3 (10 ng/ml), ascorbic acid (200 μM) and dbcAMP (0.5 mM). Cells were grown for 10-14 days and assayed by immunocytochemisty. Neural crest cells were cultured in media containing 10% fetal bovine serum and passed every 4-5 days. Osteocyte, adipocyte and chondrocyte differentiation was performed according to manufacturer directions using StemPro Osteogenesis Kit, StemPro Chondrogenesis Differentiation Kit, StemPro Adipogenesis Differentiation Kit (Invitrogen), respectively.

Immunocytochemistry and Flow Cytometry.

Cells were fixed in 4% paraformaldehyde in phosphate buffered saline (PBS) and stained with primary antibodies listed in attached Table 1 (below). Secondary antibodies were Alexa Fluor 488 and Alexa Fluor 555-conjugated (Invitrogen). DNA was visualized by staining with DAPI. For flow cytometry, one million live cells dissociated with Accutase were re-suspended in PBS and incubated for 30 minutes on ice with primary conjugated antibodies, listed in Table 1. Unconjugated p75 (neurotrophin receptor) and Hnk1 antibodies were detected with Alexa Fluor 633 and Alexa Fluor 488-conjugated secondary antibodies, respectively. Cells were analyzed using the CyAN ADP (Beckman Coulter) and FlowJo software.

Real-Time PCR and Western Blot Analysis.

RNA was extracted using the RNeasy Mini Kit (Qiagen). One microgram of total RNA was used for cDNA synthesis using the iScript cDNA kit (BioRad). 10 nanograms of cDNA were used for real-time PCR with Taqman assays (Applied Biosystems) on a MyiQ Real-time PCR iCycler (BioRad). Each sample was analyzed in duplicate and gene expression was normalized to GAPDH. For Western blot analysis, hESCs were plated in defined media and then switched to SB media alone or with addition of 5-50 ng/ml BMP4 (R&D systems) or 500 ng/ml Noggin for 3 or 6 hours. After protein extraction with RIPA buffer, ~30 μg of total protein extract were loaded in 12% SDS gels and transferred to nitrocellulose membranes and probed with antibodies for pSmad1,5,8, Smad1 (Cell Signaling Technologies) and Cdk2 (Santa Cruz Biotechnology).

In Ovo Transplantation.

Neural crest cells were passaged with Accutase then seeded on agarose-coated plates to form small-sized aggregates. Three days later cell aggregates were labeled with the fluorescent dye DiO as described (25). A slit was cut into HH stage 8-10 chick embryos in ovo at the junction of the non-neural ectoderm and the forming neural tube, and a small DiO labeled cell aggregate was inserted and positioned under a fluorescence stereomicroscope. Egg windows were sealed with transparent tape and eggs incubated for 48-72 h, after which embryos were evaluated for the presence of fluorescent cells. Embryos were photographed to document the localization of DiO labeled cells, and then fixed in freshly prepared 4% paraformaldehyde overnight at 4° C. Embryos were rinsed three times in PBS, incubated in 30% sucrose/PBS overnight at 4° C., embedded in OCT and frozen in a bath of dry ice/isopentane. 8-12 μm sections were cut and processed for immunofluorescence detection of human nuclear antigen (hNA, Chemicon; 1:100), β-tubulin isotype III (Tuj1, Sigma: 1:400) or Peripherin (Santa Cruz Biotechnology, Inc: 1:200). Sections were dried at room temperature for 10 min, rehydrated in PBS and permeabilized in PBS, 0.2% Tween 20 for 15 min. Sections were incubated with primary antibody diluted in 1% BSA/PBS, 0.1% Triton X-100 at 4° C. overnight in a humid chamber, washed three times for 10 min in PBS, 0.2% Tween 20, then incubated with a 1:200 dilution each of Cy2 conjugated goat anti-mouse IgG1 (hNA; Jackson Immunoresearch) and Cy3 conjugated goat anti-mouse IgG2b (Tuj1) or Donkey anti-Goat IgG (Peripherin) at 37° C. for 1.5 h. Sections were washed twice in PBS, 0.2% Tween 20 and finally in PBS. Some sections were stained with DAPI (5 μg/ml) in PBS for 10 min prior to applying a coverslip using Prolong Gold (Invitrogen). Fluorescence was visualized and photographed on a Zeiss AXIO microscope.

Results

Activation of the Wnt Pathway Redirects Neural Progenitors Towards a Neural Crest Fate Human pluripotent cells can be efficiently differentiated into Pax6$^+$ NPCs by simultaneous inhibition of Activin A/Nodal and BMP signaling with SB 431542 and Noggin, respectively (see FIGS. 1A and B) (12). Although Pax6$^+$ Sox1$^+$ Sox2$^+$ NPCs predominate in cultures where Smad signaling is blocked, relatively minor amounts of p75$^+$ neural crest cells are also generated under these conditions (FIGS. 1B and S1), consistent with previous findings (12).

Figure 2:
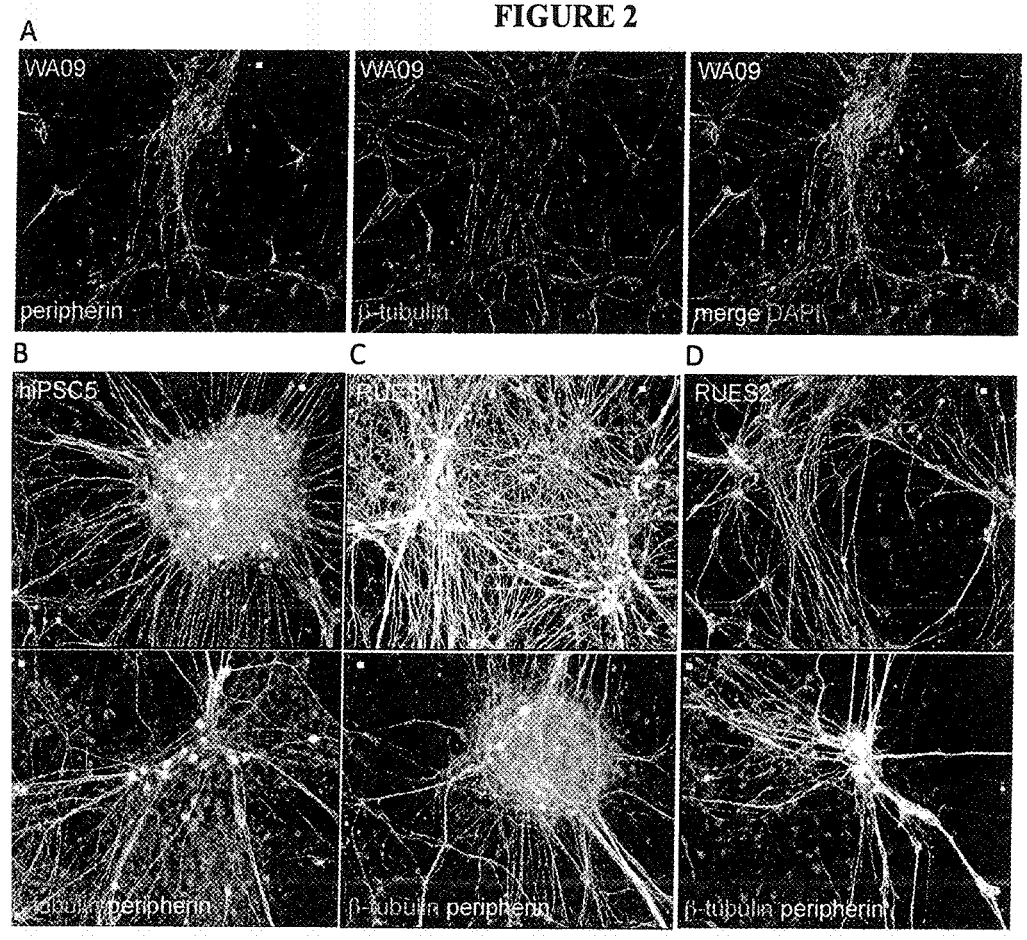
FIG. 2. shows that hESC differentiation to neural crest requires Wnt signaling and is antagonized by Activin A and BMP pathways. (A) Flow cytometry analysis of WA09 hESCs treated as indicated for 15 days. Cells were analyzed by probing with antibodies for p75 and Hnk1. (B) Immunochemistry and bright field (bottom left panel) of WA09 hESCs cells treated with 1310 and SB 431542 for 12 days, Cells were probed with antibodies as indicated; p75, Pax6, Ap2, Hnk1 and for DAP1 (DNA). Micron Bar, 100 µM. (C) RT-PCR transcript analysis of hESCs and neural crest (passage 10) cells treated with 1310 and SB 431542. Transcript levels were normalized to Gapdh control. Assays were performed in triplicate and shown as +/−standard deviation. (D) Illustration of the signaling requirements for neural crest differentiation from hESCs cells showing that activation of canonical Wnt signaling combined with low Smad2,3 and Smad1,5,8 activity are strict requirements for the efficient generation of neural crest-like cells from hESCs.

The signaling requirements that determine a NCSC versus a NPC fate have not been previously defined in culture. In the absence of a specific method that allows for the generation of highly enriched cultures of NCSCs, FACs isolation of Hnk1$^+$ p75$^+$ cells from NPC cultures has been the method of choice to obtain hESC-derived neural crest (18). Since canonical Wnt signaling performs known roles in promoting neural crest formation in vertebrate development (3-5) we asked whether concomitant activation of Wnt signaling combined with global Smad inhibition would more efficiently divert early neuroectoderm away from a NPC fate towards a neural crest-like identity. This was initially tested by addition of (2'Z,3'E)-6-Bromoindirubin-3'-oxime (BIO), a small molecule inhibitor of glycogen synthase kinase 3 (GSK3) that acts as a Wnt mimetic in a variety of contexts (19, 20). Addition of BIO to hESC cultures efficiently activates the canonical Wnt pathway, as indicated by the activation of a β-catenin-dependent luciferase reporter (FIG. S2). Concurrent Smad inhibition combined with activation of Wnt signaling (+BIO) after 12 days severely inhibited the formation of Pax6$^+$ cells while markedly increasing the percentage of p75+ cells (FIG. 1B). These cultures lost markers for pluripotent cells, such as Nanog and Oct4 (FIG. S3). Addition of Dickkopf, a Wnt antagonist, severely reduced the low level of p75$^{bright}$ cells present in NPC cultures obtained by treatment with Noggin and SB 431542 (FIG. 1C). p75$^{bright}$ cells expressed high levels of the neural crest marker Ap2 but low levels of the NPC marker Pax6 (FIG. 1D). p75$^{dim}$ cells on the other hand expressed high levels of Pax6 transcript but low levels of Ap2, indicating that p75$^{dim}$ and p75$^{bright}$ cells represent NPC and neural crest-like populations, respectively (also see FIG. 2). These data indicate that the minor population of p75$^{bright}$ neural crest-like cells in NPC cultures has a requirement for Wnt signaling (addressed in further detail below).

To establish a role for Wnt signaling in the specification of hESC-derived neural crest-like cells we performed dose-response experiments where the GSK3 inhibitor BIO or Wnt3a were added to cultures treated with SB 431542 and Noggin. Increasing the amount of BIO (0-2 □M) or recombinant Wnt3a (0-50 ng/ml) increased the proportion of Hnk1$^{bright}$ p75$^{bright}$ cells in a dose-dependent manner (FIGS. 1E and 1F). As the concentration of BIO was reduced, the proportion of p75$^{dim}$ cells increased indicating that cells were being directed to a Pax6+ p75$^{dim}$ fate (see FIG. 1C). This was confirmed by comparing p75$^{dim}$ and p75$^{bright}$ cells that were generated following treatment with an intermediate concentration of BIO (0.5 □M). qRT-PCR analysis shows that p75$^{dim}$ cells expressed elevated levels of Pax6 and Sox2 but low levels of Ap2, p75 and Slug transcripts (FIG. S4A). Conversely, p75$^{bright}$ cells show elevated levels of Ap2, p75 and Slug transcripts but low levels for Sox2 and Pax6. Immunostaining also confirmed that Sox2 expression showed a dose-dependent response to BIO when Smad signaling was suppressed, consistent with cells being directed away from a neural progenitor fate towards a neural crest-like identity at higher concentrations (FIG. S4B). As expected, pluripotent cell markers Nanog and Oct4 were lost over a broad range of BIO concentrations in the presence of SB 431542 (FIG. S4B). Elevating Wnt signaling in the context of low Smad activity therefore directs cells away from a Pax6+ p75$^{dim}$ population to a neural crest-like fate.

Next, we performed further analysis to define the signaling requirements required to efficiently specify hESC-derived Hnk1+ p75+ neural crest-like cells. Addition of SB 431542, BIO and Noggin (SBioN) generated a highly enriched Hnk1+ p75+ population but unexpectedly, omission of Noggin had no major impact (FIG. 2A), indicating that active suppression of BMP signaling is not required under our conditions. This can be explained by the low level of basal BMP-dependent Smad1,5,8 activity in these cells (FIG. S5). Addition of BMP4 to SBio-treated cultures however, suppressed the transition to an Hnk1$^{bright}$ p75$^{bright}$ state showing that BMP signaling antagonizes this pathway (FIG. 2A). Recombinant Wnt3a can substitute for BIO, when combined with SB 431542 but BIO and SB 431542 by themselves are ineffective.

To characterize the Hnk1$^{bright}$ p75$^{bright}$ cell population in further detail, immunostaining was performed using antibodies for neural crest markers p75, Ap2, Hnk1 and the NPC marker, Pax6. This showed that >90% of SB 431542 and BIO (SBio)-treated cells were positive for neural crest markers but <5% expressed Pax6 (FIG. 2B). Elevated levels of Ap2, p75, Sox9, Sox10, Pax3, Brna3 and Zicl transcripts further shows the p75+ population generated with SBio is closely related to authentic neural crest cells (FIG. 2C). hESC-derived NCSCs could be maintained as a stable, self-renewing population over extended periods of culture in SBio-containing media (>25 consecutive passages). Similar results were obtained when different hESC lines and human induced pluripotent stem cells (hiPSCs) were treated with SBio-containing media (FIGS. S6 and S7). We conclude that activation of canonical Wnt signaling combined with low Smad2,3 and Smad1,5,8 activity are strict requirements for the efficient generation of neural crest-like cells from hESCs (FIG. 2D).

Multi-Lineage Differentiation of hESC-Derived Neural Crest Cells

Figure 3:
FIG. 3. shows the peripheral neurons derived from neural crest stem cells. BIO, SB 431542-treated NCSCs were differentiated to peripherin+β-tubulin+ cells for 14 days after switching to N2-based neural differentiation media. Fixed cells were then probed with antibodies for peripherin and β-tubulin. DNA was detected by staining with DAPI. Micron bar, 100 µM.

The neural crest is a multipotent population of cells arising from neural ectoderm in vertebrate embryos, capable of forming a diverse array of cell lineages. To characterize the developmental potential of hESC-derived NCSC described in this report, we asked if they could differentiate into lineages previously shown to be generated by hESC-derived neural crest-like cells (15). These experiments were performed on NCSC that had been self-renewed for >10 passages, to establish that the developmental potential of these cells was retained over time. First, we confirmed that NCSC have the capacity for neural differentiation as previously described (12). After culture in media containing a cocktail of factors (BDNF, GDNF, NGF, neurotrophin-3 and dbcAMP) that promote neural differentiation (18), ~75% of cells expressed β-tubulin and a similar number expressed peripherin/neurofilament 4 (FIG. 3A), indicative of peripheral neurons. Similar results were obtained with two other hESC lines (RUES1 and RUES2) and hiPSCs (FIG. 3B-D).

Figure 4:
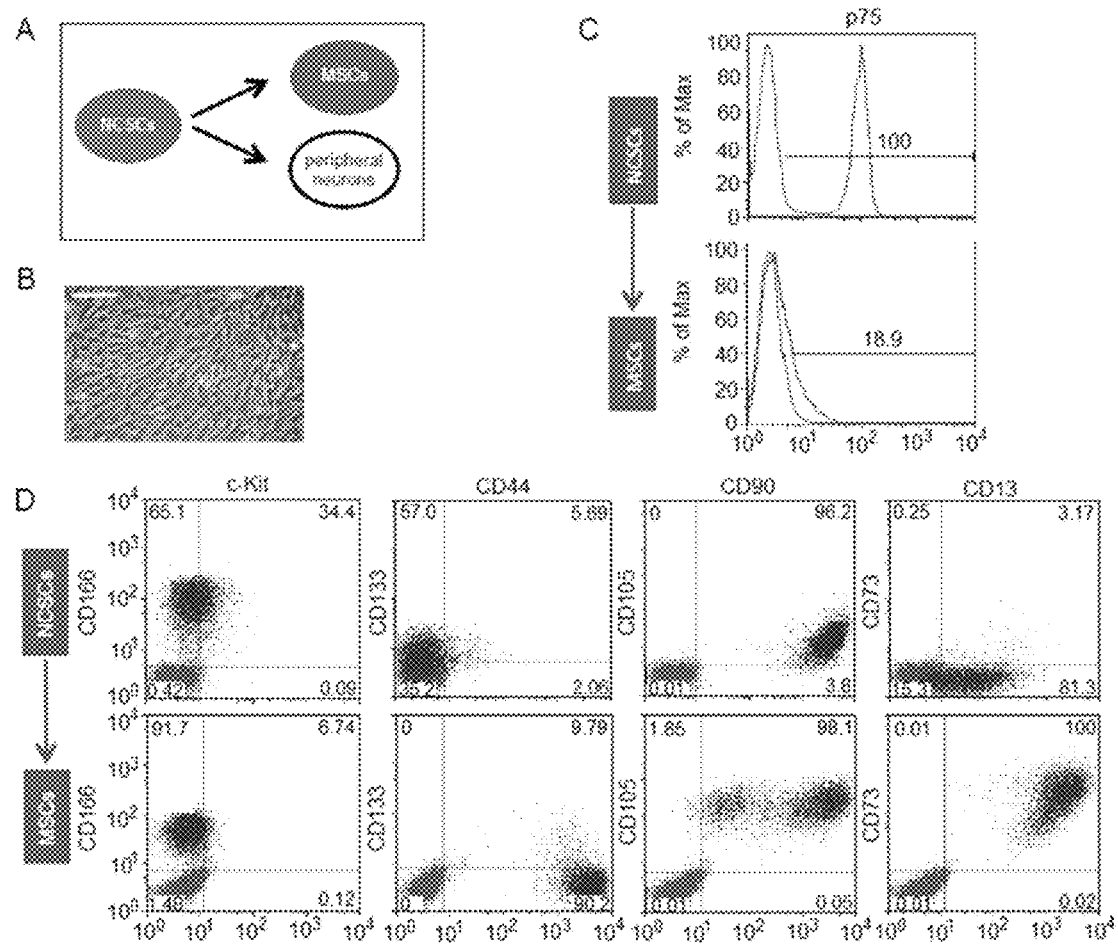
FIG. 4. shows the differentiation of neural crest cells into mesenchymal progenitors. (A) Schematic illustrating possible differentiation pathways for neural crest stem cells (NCSCs). (B) Bright field view of mesenchymal cells generated from neural crest after treatment for 4 days with 10% FBS-containing media. Micron bar, 100 µm. (C) Loss of p75 expression detected by flow cytometry as NCSCs are converted to mesenchymal cells. (D) Flow cytometry analysis showing marker expression (blue) in NCSCs and mesenchymal cells. Red, isotype control. The % of positive cells for each antigen in each quadrant is shown.
Figure 5:
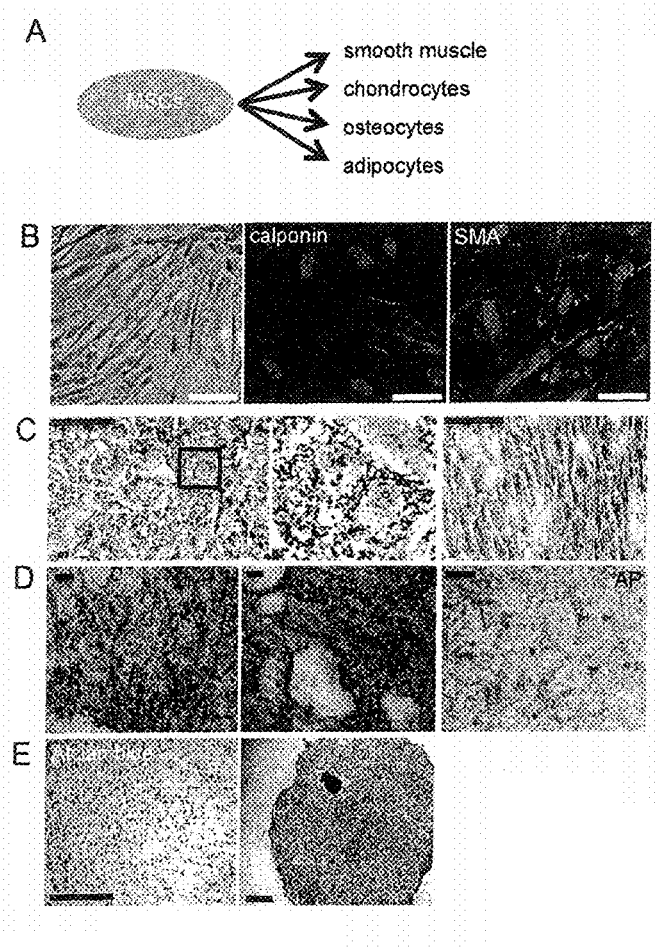
FIG. 5. shows the differentiation of neural crest derived-mesenchymal cells. (A) Schematic showing the lineages capable of being formed from neural crest-derived mesenchymal cells in culture. (B) Bright field picture (left hand panel) after differentiation into calponin+ smooth muscle actin+(SMA) smooth muscle cells. (C) Oil red O-stained adipocytes and (right hand panel) a bright field image of adipocytes showing oil droplets. (D) Osteocytes produced by differentiation of neural crest-derived mesenchymal cells, detected by staining with Alizarin Red and alkaline phosphatase (AP) staining. (E) Differentiation of mesenchymal cells to chondrocytes, detected by staining with Alcian Blue. Micron bar, 100 µm.

Neural crest cells can also form mesenchymal precursor cells in vitro (15, 21). By culturing cells in media containing 10% FBS (21, 22), we confirmed that SBio-generated NCSC can be efficiently converted to a cell type with mesenchymal properties over a 4-day period (FIG. 4A-B). Mesenchymal cells produced were highly enriched for mesenchymal stem cell (MSC) markers such as CD73, CD44, CD105, CD13 but lost expression of p75 (FIG. 4C-D). We also showed that hESC-derived mesenchymal cells could be converted into smooth muscle cells, chondrocytes, osteocytes and adipocytes (FIG. 5). Many of these observations were repeated using NCSCs derived from other hESC lines (RUES1, RUES2) and from hiPSCs (FIG. S8 and S9). In summary, neural crest-like cells generated by our highly efficient one-step method using small molecule compounds is capable of multi-lineage differentiation. This is comparable to the developmental potential of neural crest cells isolated from NPC cultures by FACS sorting reported previously (15, 18).

In Vivo Potential of hESC-Derived NCSCs

Figure 6:
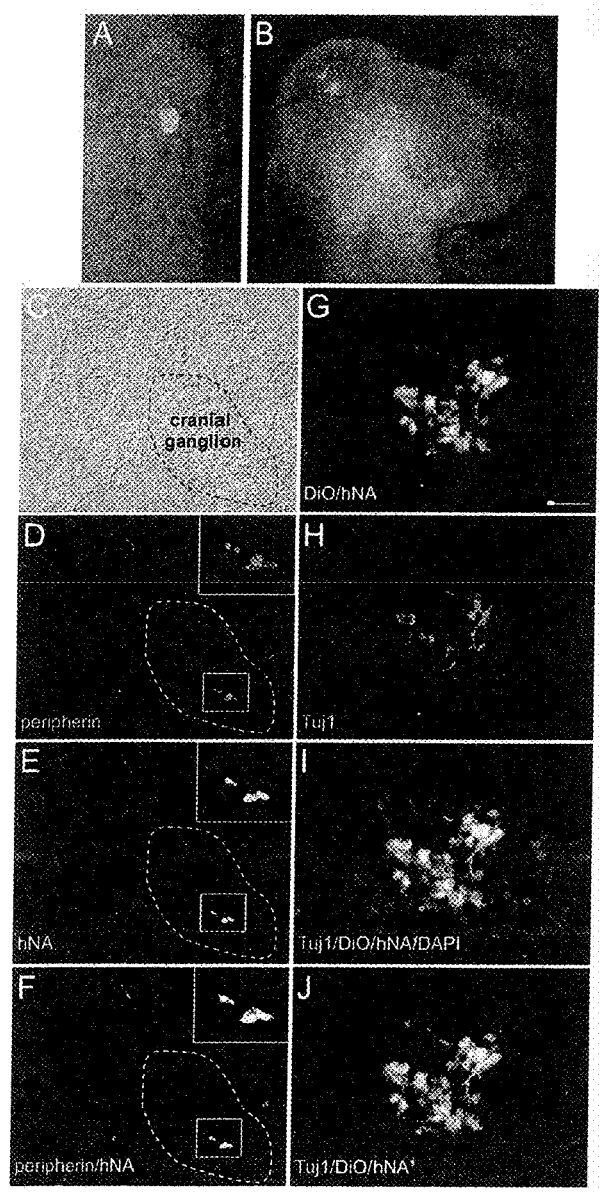
FIG. 6 shows the in vivo migration and differentiation of WA09 hESC derived NCSC. (A) DiO labeled cells at time of injection and (B) 48 hours later showing cell migration. (C-F) Immunocytochemistry and bright field images of the same microscopic field 72 hours after injection showing cells that had incorporated into a cranial ganglion area and differentiated to peripheral neurons. Cells were probed with antibodies for peripherin and hNA and counterstained with DAPI (DNA). Micron bar, 50 µm. (G-J) Images of the same microscopic field showing a cluster of human NCSC (hNA-positive) in the head mesenchyme adjacent to the neural tube. Many of the cells are also Tuj1-positive. Micron bar, 20 µm.

To assess the in vivo activity of SBio-derived neural crest, DiO-labeled cell aggregates were implanted into HH stage 8-10 chick embryos (n=26) along the boundary between the neural and non-neural ectoderm at the level of the forming forebrain and midbrain (FIG. 6A). Of the 19 embryos in which aggregates remained in place, migrating cells were observed in 13. Seventy-two hours following injection, fluorescently labeled cells were observed in the head and pharyngeal regions (FIG. 6B), including the cranial ganglion (FIG. 6C-J). The identity of cells was confirmed by staining with the human-specific nuclear antigen antibody (hNA; FIG. 6E). To confirm the developmental potential of injected NCSCs and their ability to generate peripheral neurons in vivo, we assessed hNA-positive cells for expression of the neural markers Tuj1 or peripherin. Double hNA/Tuj1 positive cells were observed in small clusters throughout the head mesenchyme (FIG. 6G-J). hNA/peripherin-positive cells were also found in the mesenchyme and incorporated into host cranial ganglia (FIG. 6C-F'). The injected cells therefore migrate and differentiate into peripheral neurons in vivo, consistent with the expected characteristics of neural crest cells.

DISCUSSION

Several reports have described the generation of neural crest cells from human pluripotent cells. These involve co-culture on PA6 or M5 feeder layers (15, 17), differentiation through an embryoid body stage (23) and differentiation along a neuroectoderm pathway using inhibitors of the Smad pathway (18). The latter represents a culture system primarily designed to generate Pax6$^+$ NPCs. Minor amounts of p75$^+$ neural crest produced in this system are likely to be a consequence of signaling heterogeneities in the culture dish. None of these approaches represents a guided approach to specifically generate neural crest cells and as a major downside, require a cell-sorting step to isolate highly enriched neural crest cell populations. This is obviously a significant obstacle that must be circumvented in order for the utility of neural crest to be fully realized in an experimental and cell therapy setting. This report is the first to describe a guided differentiation strategy specifically for the purpose of generating neural crest without significant amounts of other ectoderm-derived lineages. At the molecular level, neural crest generated by our method is indistinguishable from that generated by other methods (15, 18) and importantly, displays a similar differentiation potential.

The rationale for our directed-differentiation approach is based on the known roles of canonical Wnt signaling in neural crest formation during vertebrate development (3-5). The signaling conditions for neural crest progenitor specification from hESCs and hiPSCs involve inhibition of GSK3, an antagonist of Wnt signaling, and inhibition of Activin A/Smad signaling with SB 431542. BMP4 antagonized neural crest specification but inhibitors such as Noggin were not required due to the low basal level of Smad1,5,8 signaling in our system. The activation of Wnt signaling was sufficient to divert cells from a Pax6$^+$ NPC fate to a p75$^+$ neural crest fate, both of which require low levels of global Smad signaling. Wnt therefore controls a molecular switch that determines differential ectoderm fates arising from human pluripotent cells in culture. These results indicate that suppression of Wnt signaling with Dkk, for example, may be a useful approach to reduce contaminating neural crest from NPC cultures.

In summary, the present invention is directed to the first method for directed differentiation of human pluripotent cells towards a neural crest fate. The method is highly-efficient, cost-effective and precludes formation of contaminating Pax6$^+$ NPCs. Removing the need for FACS-assisted purification now provides a platform from which the basic biology of neural crest can be better understood and better applied to disease modeling. This new approach also establishes a new starting point for the generation of neural crest at scale for applications in tissue engineering and regenerative medicine applications.

Neural crest stem cells (NCs) can be isolated from differentiated cultures of human pluripotent stem cells but the process is inefficient and requires cell sorting to obtain a highly enriched population. No specific method for directed differentiation of human pluripotent cells towards NC has been reported prior to the present invention. This severely restricts the utility of these cells as a model for disease and development and for more applied purposes such as cell therapy and tissue engineering. In the present application, we have used small molecule compounds in a single-step method for the efficient generation of self-renewing neural crest-like stem cells (NCSCs) in chemically defined media. This approach is accomplished directly from human pluripotent cells without the need for co-culture on feeder-layers or cell sorting to obtain a highly-enriched population. Critical to this approach is the activation of canonical Wnt signaling and the concurrent suppression of the Activin A/Nodal pathway. Over an appropriate period of time, preferably about 10-14 days, pluripotent cells are efficiently specified along the neuroectoderm lineage towards p75$^+$ Hnk1$^+$ Ap2$^+$ neural crest-like cells, with little or no contamination with Pax6$^+$ neural progenitors. This cell population can be clonally amplified and maintained for >25 passages

| Name | μl/10$^6$ cells | Company | Cat. No. |
|---|---|---|---|
| CD13-APC | 10 | EBioscience | 17-0138-73 |
| CD90-APC | 5 | BD | 559869 |

(>100 days) while retaining the capacity to differentiate into peripheral neurons, smooth muscle cells and mesenchymal precursor cells. NCSC-derived mesenchymal precursors have the capacity for differentiation into osteocytes, chondrocytes and adipocytes. In sum, the present inventors have developed methods for the efficient generation of self-renewing neural crest stem cells that greatly enhance their potential utility in disease modeling and regenerative medicine.

TABLE 1

Source and other details relating to antibodies used in the study.

| Name | | Company | Cat. No. |
|---|---|---|---|
| CD166-PE | 20 | BD | 559263 |
| CD133-PE | 5 | EBioscience | 12-1338-42 |
| CD73-PE | 20 | | |
| CD105-PE | 5 | EBioscience | 12-1057-42 |
| cKIT-APC | 10 | BD | 341096 |
| CD44-APC | 0.33 | EBIOS | 17-0441-82 |
| p75 | 0.4 | Advance targeting systems | ABN07 |
| HNK1 | 0.4 | Sigma | C6608 |

| Name | Dilution for staining | Company | Cat. No. |
|---|---|---|---|
| p75 | 1:100 | Advance targeting systems | ABN07 |
| HNK1 | 1:300 | Sigma | C6608 |
| B-Tubulin | 1:500 | Sigma | T8660 |
| AP2 | 1:50 | DSHB | 3B5 |
| Pax6 | 1:200 | DSHB | PAX6 |
| Sox1 | 1:100 | R&D | AF3369 |
| Sox2 | 1:200 | R&D | MAB2018 |
| Peripherin | 1:200 | Chemicon | AB1530 |
| OCT3/4 | 1:200 | Santa Cruz | SC-8628 |
| Nanog | 1:200 | ReproCell | RCAB0004P-F |
| Calponin | 1:100 | Sigma | C2687 |
| SMA (Actin α-smooth muscle) | 1:100 | Sigma | A2547 |

REFERENCES

1. Selleck M A & Bronner-Fraser M (1996) The genesis of avian neural crest cells: a classic embryonic induction. (Translated from eng) *Proc Natl Acad Sci USA* 93(18): 9352-9357 (in eng).
2. Meulemans D & Bronner-Fraser M (2004) Gene-regulatory interactions in neural crest evolution and development. (Translated from eng) *Dev Cell* 7(3):291-299 (in eng).

3. Garcia-Castro M I, Marcelle C, & Bronner-Fraser M (2002) Ectodermal Wnt function as a neural crest inducer. (Translated from eng) Science 297(5582):848-851 (in eng).
4. Patthey C, Edlund T, & Gunhaga L (2009) Wnt-regulated temporal control of BMP exposure directs the choice between neural plate border and epidermal fate. (Translated from eng) Development 136(1):73-83 (in eng).
5. Wilson S I, et al. (2001) The status of Wnt signalling regulates neural and epidermal fates in the chick embryo. (Translated from eng) Nature 411(6835):325-330 (in eng).
6. Bonstein L, Elias S, & Frank D (1998) Paraxial-fated mesoderm is required for neural crest induction in Xenopus embryos. (Translated from eng) Dev Biol 193(2):156-168 (in eng).
7. Liem K F, Jr., Tremml G, Roelink H, & Jessell T M (1995) Dorsal differentiation of neural plate cells induced by BMP-mediated signals from epidermal ectoderm. (Translated from eng) Cell 82(6):969-979 (in eng).
8. Monsoro-Burq A H, Fletcher R B, & Harland R M (2003) Neural crest induction by paraxial mesoderm in Xenopus embryos requires FGF signals. (Translated from eng) Development 130(14):3111-3124 (in eng).
9. Marchant L, Linker C, Ruiz P, Guerrero N, & Mayor R (1998) The inductive properties of mesoderm suggest that the neural crest cells are specified by a BMP gradient. (Translated from eng) Dev Biol 198(2):319-329 (in eng).
10. LaBonne C & Bronner-Fraser M (1998) Neural crest induction in Xenopus: evidence for a two-signal model. (Translated from eng) Development 125(13):2403-2414 (in eng).
11. Koch P, Opitz T, Steinbeck J A, Ladewig J, & Brustle O (2009) A rosette-type, self-renewing human ES cell-derived neural stem cell with potential for in vitro instruction and synaptic integration. (Translated from eng) Proc Natl Acad Sci USA 106(9):3225-3230 (in eng).
12. Chambers S M, et al. (2009) Highly efficient neural conversion of human ES and iPS cells by dual inhibition of SMAD signaling. (Translated from eng) Nat Biotechnol 27(3):275-280 (in eng).
13. Elkabetz Y, et al. (2008) Human ES cell-derived neural rosettes reveal a functionally distinct early neural stem cell stage. (Translated from eng) Genes Dev 22(2):152-165 (in eng).
14. Li X J, et al. (2005) Specification of motoneurons from human embryonic stem cells. (Translated from eng) Nat Biotechnol 23(2):215-221 (in eng).
15. Lee G, et al. (2007) Isolation and directed differentiation of neural crest stem cells derived from human embryonic stem cells. (Translated from eng) Nat Biotechnol 25(12):1468-1475 (in eng).
16. Lee G & Studer L (2010) Induced pluripotent stem cell technology for the study of human disease. (Translated from eng) Nat Methods 7(1):25-27 (in eng).
17. Jiang X, et al. (2009) Isolation and characterization of neural crest stem cells derived from in vitro-differentiated human embryonic stem cells. (Translated from eng) Stem Cells Dev 18(7):1059-1070 (in eng).
18. Lee G, Chambers S M, Tomishima M J, & Studer L (2010) Derivation of neural crest cells from human pluripotent stem cells. (Translated from eng) Nat Protoc 5(4):688-701 (in eng).
19. Meijer L, Flajolet M, & Greengard P (2004) Pharmacological inhibitors of glycogen synthase kinase 3. (Translated from eng) Trends Pharmacol Sci 25(9):471-480 (in eng).
20. Sato N, Meijer L, Skaltsounis L, Greengard P, & Brivanlou A H (2004) Maintenance of pluripotency in human and mouse embryonic stem cells through activation of Wnt signaling by a pharmacological GSK-3-specific inhibitor. (Translated from eng) Nat Med 10(1):55-63 (in eng).
21. Barberi T, Willis L M, Socci N D, & Studer L (2005) Derivation of multipotent mesenchymal precursors from human embryonic stem cells. (Translated from eng) PLoS Med 2(6):e161 (in eng).
22. Barberi T, et al. (2007) Derivation of engraftable skeletal myoblasts from human embryonic stem cells. (Translated from eng) Nat Med 13(5):642-648 (in eng).
23. Zhou Y & Snead M L (2008) Derivation of cranial neural crest-like cells from human embryonic stem cells. (Translated from eng) Biochem Biophys Res Commun 376(3):542-547 (in eng).
24. Singh A M, et al. (2007) Chibby, an antagonist of the Wnt/beta-catenin pathway, facilitates cardiomyocyte differentiation of murine embryonic stem cells. (Translated from eng) Circulation 115(5):617-626 (in eng).
25. Darnell D K, Garcia-Martinez V, Lopez-Sanchez C, Yuan S, & Schoenwolf G C (2000) Dynamic labeling techniques for fate mapping, testing cell commitment, and following living cells in avian embryos. (Translated from eng) Methods Mol Biol 135:305-321 (in eng).

The invention claimed is:

1. A method of producing p75+ Hnk1+ Ap2+ multipotent neural crest-like cells from human embryonic stem cells (hESCs) or human induced pluripotent stem cells (hiPSCs) comprising differentiating said stem cells in a differentiation medium in the absence of feeder cells consisting essentially of an effective amount of a glycogen synthase kinase (GSK) inhibitor in combination with an effective amount of an Activin A inhibitor to produce a population of cells comprising p75+ Hnk1+ Ap2+ multipotent neural crest-like stem cells and PAX6+ neural progenitor cells, wherein said GSK inhibitor is (2'Z,3'E)-6-Bromoindimbin-3'-oxime (BIO) and said Activin A inhibitor is SB 431542 and wherein said PAX6+ neural progenitor cells produced comprise no more than 10% of the total population of p75+ Hnk1+ Ap2+ multipotent neural crest-like cells and PAX6+ neural progenitor cells; and optionally isolating said neural p75+ Hnk1+ Ap2+ multipotent neural crest-like cells from said population of cells.

2. The method according to claim 1 wherein hESCs are differentiated into said neural p75+ Hnk1+ Ap2+ multipotent neural crest-like cells.

3. The method according to claim 1 wherein hiPSCs are differentiated into said neural p75+ Hnk1+ Ap2+ multipotent neural crest-like cells.

4. The method according to claim 1 wherein said neural p75+ Hnk1+ Ap2+ multipotent neural crest-like cells are isolated from said population of cells.

5. The method according to claim 2 wherein said neural p75+ Hnk1+ Ap2+ multipotent neural crest-like cells are isolated from said population of cells.

6. The method according to claim 3 wherein said neural p75+ Hnk1+ Ap2+ multipotent neural crest-like cells are isolated from said population of cells.

7. The method according to claim 1 wherein said differentiation medium further includes an effective amount of at least one bone morphogenic inhibitor selected from the group consisting of noggin, chordin, sclerostin, follistatin, gremlin, dorsomorphin and connective tissue growth factor (CTFG).

8. The method according to claim 2 wherein said differentiation medium further includes an effective amount of at least one hone morphogenic inhibitor selected from the group consisting of noggin, chordin, sclerostin, follistatin, gremlin, dorsomorphorin and connective tissue growth factor (CTFG).

9. The method according to claim 3 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

10. The method according to claim 4 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

11. The method according to claim 5 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

12. The method according to claim 6 wherein said differentiation medium further includes an effective amount of at least one bone morphogenic inhibitor selected from the group consisting of noggin, chordin, sclerostin, follistatin, gremlin, dorsomorphorin and connective tissue growth factor (CFTG).

13. A method of producing p75+ Hnk1+ Ap2+ multipotent neural crest-like cells from human embryonic stem cells (hESCs) or human induced pluripotent stem cells (hiPSCs) comprising differentiating said stem cells in a differentiation medium in the absence of feeder cells consisting essentially of an effective amount of a Wnt protein in combination with an effective amount of an Activin A inhibitor to produce a population of cells comprising p75+ Hnk1+ Ap2+ multipotent neural crest-like stem cells and PAX6+ neural progenitor cells, wherein said Wnt protein is Wnt3a and said Activin A inhibitor is SB 431542 and wherein said PAX6+ neural progenitor cells produced comprise no more than 10% of the total population of p75+ Hnk1+ Ap2+ multipotent neural crest-like cells and PAX6+ neural progenitor cells; and optionally isolating said neural p75+ Hnk1+ Ap2+ multipotent neural crest-like cells from said population of cells.

14. The method according to claim 13 wherein hESCs are differentiated into said neural p75+ Hnk1+ Ap2+ multipotent neural crest-like cells.

15. The method according to claim 13 wherein hiPSCs are differentiated into said neural p75+ Hnk1+ Ap2+ multipotent neural crest-like cells.

16. The method according to claim 13 wherein said neural p75+ Hnk1+ Ap2+ multipotent neural crest-like cells are isolated from said population of cells.

17. The method according to claim 14 wherein said neural p75+ Hnk1+ Ap2+ multipotent neural crest-like cells are isolated from said population of cells.

18. The method according to claim 15 wherein said neural p75+ Hnk1+ Ap2+ multipotent neural crest-like cells are isolated from said population of cells.

19. The method according to claim 13 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

20. The method according to claim 14 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

21. The method according to claim 15 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

22. The method according to claim 16 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

23. The method according to claim 17 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

24. The method according to claim 18 wherein said differentiation medium further includes an effective amount of at least one bone morphogenic inhibitor selected from the group consisting of noggin, chordin, sclerostin, follistatin, gremlin, dorsomorphorin and connective tissue growth factor (CTFG).

\* \* \* \* \*